(12) United States Patent
Bender et al.

(10) Patent No.: US 12,194,229 B2
(45) Date of Patent: Jan. 14, 2025

(54) PORTABLE HOLDING CHAMBER

(71) Applicant: Trudell Medical International Inc., London (CA)

(72) Inventors: Sam Bender, Thornhill (CA); Adam Meyer, London (CA); Michael Nuttall, London (CA)

(73) Assignee: TRUDELL MEDICAL INTERNATIONAL INC., London (CA)

( * ) Notice: Subject to any disclaimer, the term of this patent is extended or adjusted under 35 U.S.C. 154(b) by 1119 days.

(21) Appl. No.: 16/932,237

(22) Filed: Jul. 17, 2020

(65) Prior Publication Data

US 2021/0154419 A1 May 27, 2021

Related U.S. Application Data

(60) Provisional application No. 62/878,079, filed on Jul. 24, 2019.

(51) Int. Cl.
| | |
|---|---|
| *A61M 15/00* | (2006.01) |
| *A61M 11/00* | (2006.01) |
| *A61M 16/20* | (2006.01) |

(52) U.S. Cl.
CPC ...... *A61M 15/0026* (2014.02); *A61M 15/009* (2013.01)

(58) Field of Classification Search
CPC .......... A61M 15/0088; A61M 15/0026; A61M 15/009; A61M 11/002; A61M 15/008; A61M 16/208; A61M 2202/0216; A61M 2205/07; A61M 2205/14; A61M 2205/276; A61M 2205/3313; A61M 2205/332; A61M 2205/3331; A61M 2205/3375; A61M 2205/3389; A61M 2205/3553; A61M 2205/3569; A61M 2205/3592;
(Continued)

(56) References Cited

U.S. PATENT DOCUMENTS

| | | |
|---|---|---|
| 3,565,071 A | 2/1971 | Cobb |
| 3,789,843 A | 2/1974 | Armstrong et al. |

(Continued)

FOREIGN PATENT DOCUMENTS

| | | |
|---|---|---|
| EP | 0 028 929 B1 | 5/1984 |
| EP | 0 075 548 B1 | 7/1986 |

(Continued)

OTHER PUBLICATIONS

Written Opinion for International Application No. PCT/IB2020/056754 mailed Oct. 30, 2020 (11 pages).
(Continued)

*Primary Examiner* — Kendra D Carter
*Assistant Examiner* — Mautin I Ashimiu
(74) *Attorney, Agent, or Firm* — Crowell & Moring LLP

(57) ABSTRACT

A medication delivery system having a holding chamber capable of delivering dosages of medicament from a metered dose inhaler. The holding chamber includes a first housing component having a user interface with an outlet opening and a second housing component having an inlet opening spaced apart from the outlet opening of the first housing component. The first housing component is pivotally connected to the second housing component about a pivot axis.

20 Claims, 32 Drawing Sheets

(58) Field of Classification Search
CPC ........ A61M 2205/505; A61M 2205/52; A61M 2205/583; A61M 2205/587; A61M 2205/8212; A61M 2206/20; A61M 2209/06; A61M 2209/10; A61M 15/0016; A61M 15/0018; A61M 15/0086
See application file for complete search history.

(56) References Cited

U.S. PATENT DOCUMENTS

| | | |
|---|---|---|
| 3,865,279 A | 2/1975 | James |
| 3,994,421 A | 11/1976 | Hansen |
| 4,470,412 A | 9/1984 | Nowacki et al. |
| 4,509,515 A * | 4/1985 | Altounyan ........ A61M 15/0023 128/200.23 |
| 4,534,343 A | 8/1985 | Nowacki et al. |
| 4,641,644 A | 2/1987 | Andersson et al. |
| 4,678,106 A | 7/1987 | Newell et al. |
| 4,809,692 A | 3/1989 | Nowacki et al. |
| 4,969,578 A | 11/1990 | Gander et al. |
| 5,002,214 A | 3/1991 | Caranci |
| 5,012,803 A | 5/1991 | Foley et al. |
| 5,012,804 A | 5/1991 | Foley et al. |
| D355,029 S | 1/1995 | Kinneir et al. |
| 5,385,140 A | 1/1995 | Smith |
| D368,364 S | 4/1996 | Reitano et al. |
| 5,505,194 A | 4/1996 | Adjei et al. |
| 5,730,118 A | 3/1998 | Hermanson |
| 5,816,240 A | 10/1998 | Komesaroff |
| 5,826,571 A | 10/1998 | Casper et al. |
| 5,833,066 A | 11/1998 | Hargus et al. |
| 5,839,430 A * | 11/1998 | Cama ................ A61B 5/411 128/200.14 |
| 5,848,588 A | 12/1998 | Foley et al. |
| 5,855,307 A | 1/1999 | Biddick et al. |
| 6,026,807 A * | 2/2000 | Puderbaugh ...... A61M 15/0016 128/200.14 |
| 6,039,042 A | 3/2000 | Sladek |
| 6,056,118 A | 5/2000 | Hargus et al. |
| 6,164,275 A | 12/2000 | Van Iderstine |
| 6,196,431 B1 | 3/2001 | Underhill |
| 6,230,704 B1 * | 5/2001 | Durkin ............. A61M 15/0086 128/200.22 |
| 6,257,231 B1 | 7/2001 | Shick et al. |
| 6,293,279 B1 | 9/2001 | Schmidt et al. |
| 6,345,617 B1 | 2/2002 | Engelbreth et al. |
| 6,435,177 B1 | 8/2002 | Schmidt et al. |
| 6,557,737 B1 | 5/2003 | Hanson |
| 6,581,804 B1 | 6/2003 | Ciavarella et al. |
| 6,604,522 B2 * | 8/2003 | Arvidsson ......... A61M 15/0036 239/102.1 |
| 6,672,304 B1 | 1/2004 | Casper et al. |
| 6,685,068 B1 | 2/2004 | Thompson et al. |
| 6,729,324 B2 | 5/2004 | Casper et al. |
| D493,883 S | 8/2004 | Harvey et al. |
| D496,456 S | 9/2004 | Harvey et al. |
| 6,820,612 B2 | 11/2004 | Harabin |
| D501,552 S | 2/2005 | Harvey et al. |
| 6,904,908 B2 | 6/2005 | Bruce et al. |
| 6,907,877 B2 | 6/2005 | Balogh, II |
| 7,032,782 B1 | 4/2006 | Ciavarella et al. |
| 7,077,129 B2 | 7/2006 | Anderson et al. |
| 7,082,943 B1 | 8/2006 | Clark |
| 7,201,165 B2 | 4/2007 | Bruce et al. |
| 7,252,087 B2 | 8/2007 | Wachtel |
| 7,318,435 B2 | 1/2008 | Pentafragas |
| 7,360,537 B2 | 4/2008 | Snyder et al. |
| D576,724 S | 9/2008 | Jensen et al. |
| 7,552,728 B2 | 6/2009 | Bonney et al. |
| 7,562,656 B2 | 7/2009 | Gallem et al. |
| 7,694,676 B2 | 4/2010 | Wachtel |
| 7,748,385 B2 | 7/2010 | Lieberman et al. |
| 7,775,211 B2 | 8/2010 | Wilson |
| D623,737 S | 9/2010 | Barker et al. |
| 7,984,830 B2 | 7/2011 | Stradella |
| 8,074,641 B2 | 12/2011 | Gallem et al. |
| 8,074,642 B2 | 12/2011 | Bruce et al. |
| 8,141,551 B2 | 3/2012 | Wachter |
| 8,251,059 B2 | 8/2012 | Nishibayashi et al. |
| 8,281,784 B2 | 10/2012 | Wachtel |
| 8,308,028 B2 | 11/2012 | Bacon |
| D677,377 S | 3/2013 | White |
| 8,397,713 B2 | 3/2013 | Wachter |
| 8,397,771 B2 | 3/2013 | Geser et al. |
| 8,459,252 B2 | 6/2013 | Gallem et al. |
| 8,528,543 B2 | 9/2013 | Barney et al. |
| 8,539,947 B2 | 9/2013 | Kuhn et al. |
| 8,550,067 B2 | 10/2013 | Bruce et al. |
| 8,746,244 B2 | 6/2014 | Kaemper et al. |
| D717,425 S | 11/2014 | Von Schuckmann |
| 8,973,571 B1 | 3/2015 | Gallem et al. |
| D733,288 S | 6/2015 | Althorpe et al. |
| 9,050,433 B2 | 6/2015 | Lamble et al. |
| D739,522 S | 9/2015 | Von Schuckmann |
| 9,156,048 B2 | 10/2015 | Le Maner |
| 9,308,335 B2 | 4/2016 | Gallem et al. |
| 9,360,400 B2 | 6/2016 | Farina et al. |
| 9,364,621 B2 | 6/2016 | Von Hollen et al. |
| 9,486,592 B2 | 11/2016 | Esteve et al. |
| 9,604,017 B2 | 3/2017 | Hoelz et al. |
| 9,700,689 B2 | 7/2017 | Bruce et al. |
| 9,808,818 B2 | 11/2017 | Le Maner |
| 9,814,849 B2 | 11/2017 | Bruce et al. |
| 9,849,255 B2 | 12/2017 | Bilgic |
| D816,208 S | 4/2018 | Bhide et al. |
| 9,931,481 B2 | 4/2018 | Engelbreth |
| 10,010,687 B2 | 7/2018 | Von Schuckmann |
| 10,143,812 B2 | 12/2018 | Engelbreth |
| 10,195,373 B2 | 2/2019 | Althorpe et al. |
| 10,245,396 B2 | 4/2019 | Steelman et al. |
| 10,286,162 B2 | 5/2019 | Ciancone et al. |
| 10,335,561 B2 | 7/2019 | Krüger |
| 10,406,302 B2 | 9/2019 | Andrade et al. |
| 10,589,040 B1 | 3/2020 | Hyde et al. |
| 2002/0073992 A1 * | 6/2002 | Andersson ........ A61M 15/0091 128/204.26 |
| 2003/0010337 A1 * | 1/2003 | Anderson ........... A61M 15/009 128/200.23 |
| 2003/0141325 A1 | 7/2003 | Balogh, II |
| 2003/0205229 A1 | 11/2003 | Crockford et al. |
| 2004/0134488 A1 | 7/2004 | Davies |
| 2004/0237961 A1 | 12/2004 | Snow et al. |
| 2006/0032495 A1 | 2/2006 | Fernandez |
| 2006/0071027 A1 | 4/2006 | Davies et al. |
| 2006/0107949 A1 | 5/2006 | Davies et al. |
| 2006/0169280 A1 * | 8/2006 | Yama ................ A61M 15/0033 128/205.21 |
| 2006/0191532 A1 | 8/2006 | Ross |
| 2006/0254584 A1 | 11/2006 | Wachtel |
| 2006/0278225 A1 | 12/2006 | MacMichael et al. |
| 2008/0087279 A1 | 4/2008 | Tieck et al. |
| 2008/0132833 A1 | 6/2008 | Harding et al. |
| 2008/0257345 A1 | 10/2008 | Snyder et al. |
| 2010/0071688 A1 | 3/2010 | Dwyer |
| 2010/0083963 A1 | 4/2010 | Wharton et al. |
| 2010/0163042 A1 | 7/2010 | Bhowmick et al. |
| 2011/0232636 A1 | 9/2011 | Von Hollen et al. |
| 2012/0211007 A1 | 8/2012 | Zierenberg |
| 2014/0000588 A1 | 1/2014 | Le Maner |
| 2015/0096563 A1 | 4/2015 | Toksoz et al. |
| 2016/0022933 A1 | 1/2016 | Ciancone et al. |
| 2016/0166787 A1 | 6/2016 | Morrison et al. |
| 2016/0279355 A1 | 9/2016 | Malhotra et al. |
| 2016/0375207 A1 | 12/2016 | Bhide et al. |
| 2017/0056608 A1 | 3/2017 | McDerment et al. |
| 2017/0326313 A1 | 11/2017 | Clarke et al. |
| 2017/0333645 A1 | 11/2017 | Alizoti et al. |
| 2018/0344956 A1 | 12/2018 | Huang et al. |
| 2019/0262556 A1 | 8/2019 | Ciancone et al. |

(56) References Cited

U.S. PATENT DOCUMENTS

2019/0269866 A1 9/2019 Von Schuckmann
2020/0376210 A1* 12/2020 Simpson ................. A24F 40/44

FOREIGN PATENT DOCUMENTS

| EP | 0 134 847 B1 | 5/1987 |
| EP | 0 514 085 B1 | 7/1997 |
| EP | 0 585 379 B1 | 9/1998 |
| EP | 1 558 313 B1 | 2/2007 |
| GB | 2 363 991 A | 1/2002 |
| JP | 58-155869 | 9/1983 |
| JP | 2018-520803 | 8/2018 |
| WO | WO 91/06333 A1 | 5/1991 |
| WO | WO 03/063754 A1 | 8/2003 |
| WO | WO 2004/041670 A1 | 5/2004 |
| WO | WO 2008/040062 A1 | 4/2008 |
| WO | WO 2011/083377 A1 | 7/2011 |
| WO | WO 2012/047182 A2 | 4/2012 |
| WO | WO 2017/005420 A1 | 1/2017 |
| WO | WO 2019/081883 A1 | 5/2019 |

OTHER PUBLICATIONS

Japanese Office Action for Application No. 2022-504262 mailed Feb. 19, 2024 including English translation (7 pages).

* cited by examiner

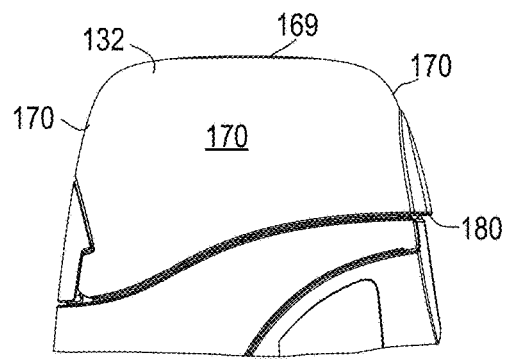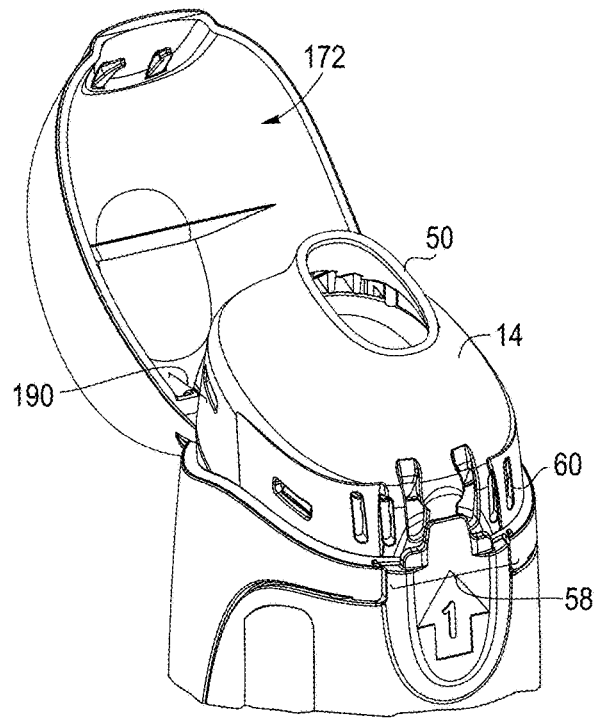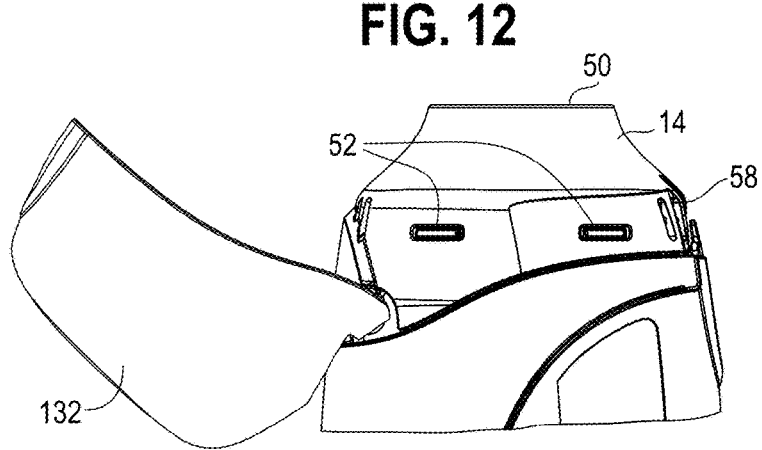

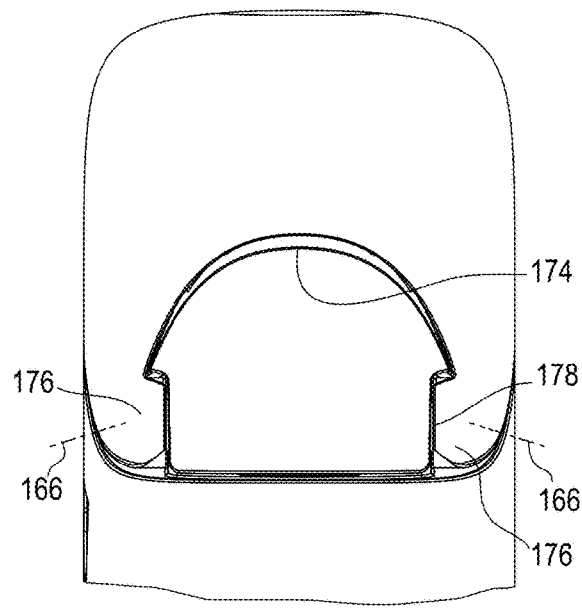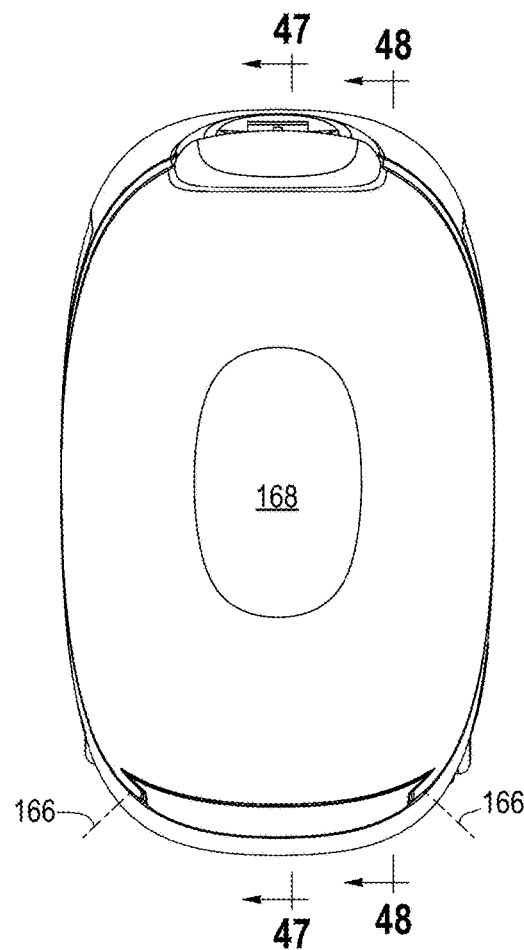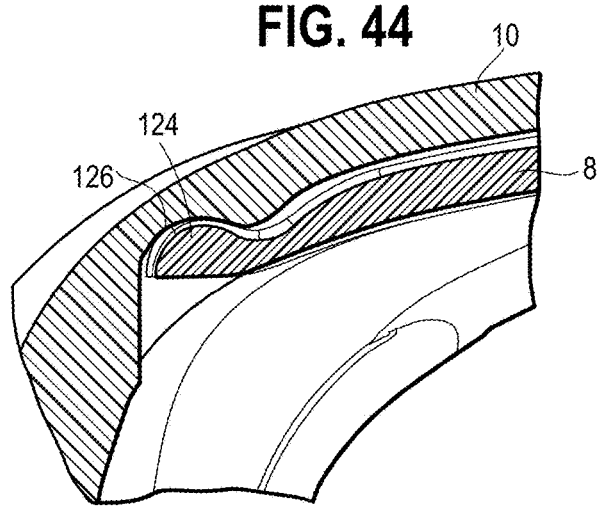

FIG. 49
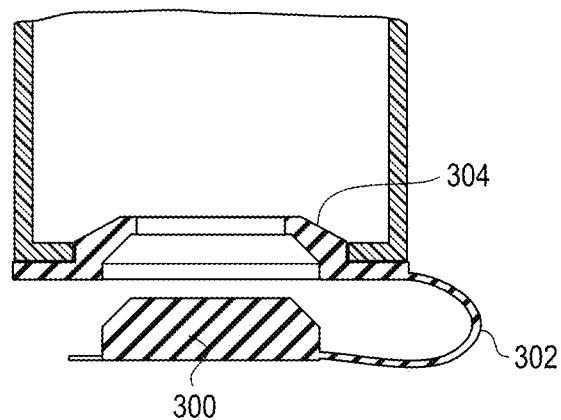
FIG. 50
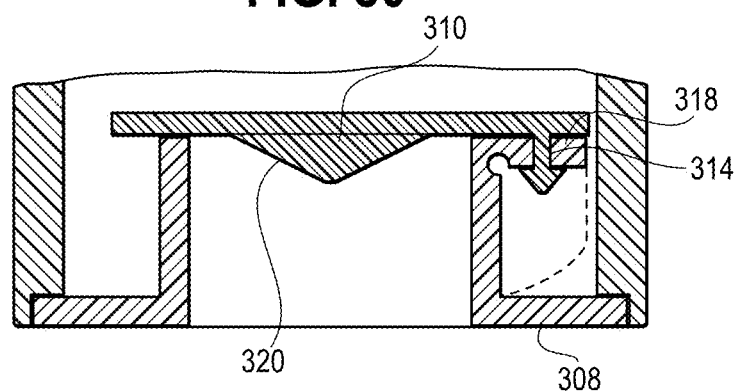
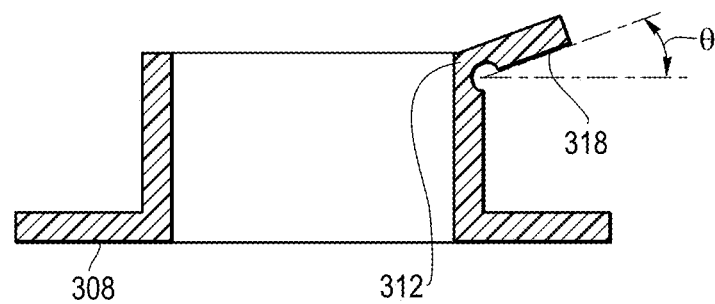

FIG. 60
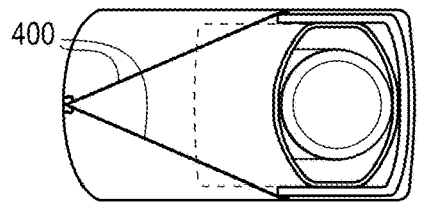
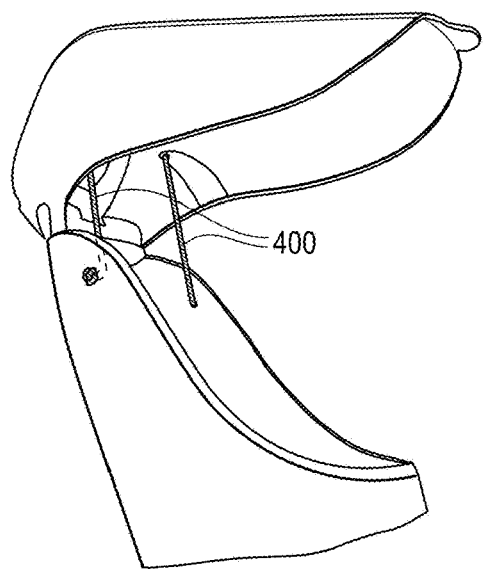
FIG. 61
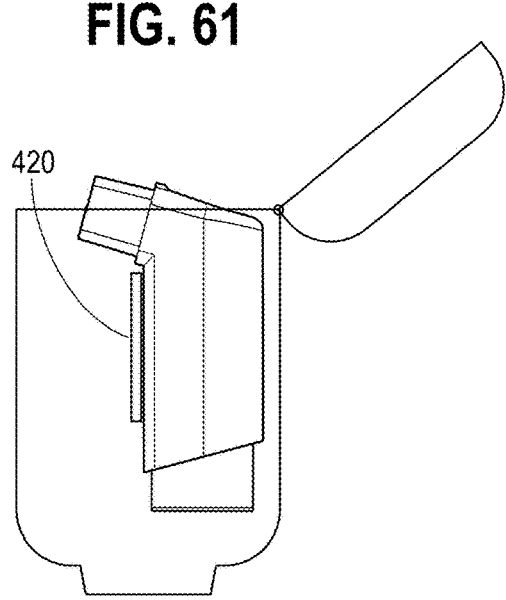
FIG. 62
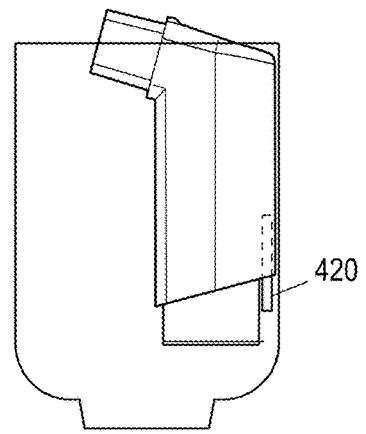

PORTABLE HOLDING CHAMBER

This application claims the benefit of U.S. Provisional Application No. 62/878,079, filed Jul. 24, 2019, the entire disclosure of which is hereby incorporated herein by reference.

FIELD OF THE INVENTION

This application is directed to a holding chamber, and in particular to a portable valved holding chamber (VHC) that encloses and carries an associated pressurized metered dose inhaler (MDI).

BACKGROUND

VHC and MDI systems are typically used to treat such conditions as asthma, COPD and cystic fibrosis. Use of only a MDI may not maximize or provide effective relief during an asthma exacerbation, and patients may not have confidence that the MDI, especially a rescue inhaler, is always working. While the combined use of a VHC with an MDI improves the effectiveness of the MDI, users often do not carry a VHC due to the size of most commercially available VHC's. At the same time, the volume and/or length of the VHC are correlated to the aerosol output of the VHC, meaning the configuration of the VHC must remain suitable for proper medication delivery.

In addition, many commercially available VHC's are stored separately from the MDI, thereby requiring the user to carry and locate two delivery devices, which may not be feasible when experiencing an asthma attack, for example. Locating an MDI and VHC may be even more difficult at night, or in low-lighted environments, especially where the MDI or VHC may be located in a bag. Prescription of VHC's by healthcare providers, and compliance by the patient, would likely increase with the availability of a relatively small and portable VHC, especially if the VHC was capable of storing the MDI between uses.

BRIEF SUMMARY

In one aspect, one embodiment of a holding chamber includes a first housing component having a user interface with an outlet opening and a second housing component having an inlet opening spaced apart from the outlet opening of the first housing component. The first housing component is pivotally connected to the second housing component about a pivot axis. The first and second housing components are pivotable relative to each other about the pivot axis between a closed configuration, wherein the first and second housing components define an enclosed interior space, and an open configuration, wherein the first and second housing components define an access opening communicating with the interior space.

In another aspect, one embodiment of the holding chamber includes a cap moveably connected to one of the first and second housing components, wherein the cap is moveable between a closed position, wherein the cap engages the other of the first and second housing component and maintains the first and second housing components in the closed configuration, and an open position, wherein the cap is disengaged from the other of the first and second housing component such that the first and second housing components are capable of being pivoted to the open configuration.

In yet another aspect, one embodiment of a sealable backpiece for a holding chamber includes a flexible membrane having a plurality of flexible sections separated by a plurality of slits, wherein the flexible sections are moveable relative to each other from a closed configuration, wherein the flexible sections are positioned proximate each other, and an open configuration, wherein the flexible sections are deformed to define an inlet opening, wherein the slits define the only opening through the flexible membrane in the closed configuration.

In yet another aspect, one embodiment of a method of using a medicament delivery system includes moving a first housing component relative to a second housing component from a closed configuration to an open configuration, wherein the first housing component has a user interface including an outlet opening, and wherein the second housing component has an inlet opening spaced apart from the outlet opening of the first housing component. The method further includes removing a pressurized metered dose inhaler disposed between the first and second housing components through an access opening defined between the first and second housing components in the open configuration, moving the first and second housing components from the open configuration to the closed configuration and thereby forming an enclosed interior chamber, inserting a portion of the inhaler through the inlet opening, and dispensing a medicament from the inhaler into the interior chamber defined by the first and second housing components arranged in the closed configuration.

In yet another aspect, one embodiment of a holding chamber includes a housing component having a user interface end portion defining an outlet opening and an elliptically shaped valve seat having an outer peripheral edge. An inhalation valve includes a central elliptically shaped opening defining an inner peripheral edge overlying the outer peripheral edge of the valve seat. The inhalation valve is moveable between an inhalation configuration, wherein at least a portion of the inner peripheral edge is spaced apart from the outer peripheral edge, and an exhalation configuration, wherein the inner peripheral edge engages the outer peripheral edge.

The various aspects and embodiments provide significant advantages over conventional holding chambers. For example and without limitation, the holding chamber may house the MDI in a stored position, which protects the MDI. The holding chamber completely encapsulates the MDI and retains it in a tight, rattle free arrangement. In one embodiment, the holding chamber is water resistant. At the same time, the holding chamber may be quickly and easily opened to provide access to the MDI, which can be quickly removed from the interior space and inserted through the back piece for use by the patient. The cap maintains the holding chamber in the closed configuration, and prevents inadvertent opening thereof, for example if inadvertently dropped, while also covering the mouthpiece inlet opening and preventing contamination of the interior space of the holding chamber.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

The Figures show different embodiments of medication delivery systems, holding chambers and methods for use and assembly thereof.

FIG. 10 is a side view of a user interface with a cap in a closed position.

FIG. 11 is a perspective view of a user interface with a cap in an open position.

FIG. 12 is a side view of the user interface with the cap in an open position.

FIG. 42 shows a partial end view of the cap in a closed configuration.

FIG. 43 shows a top view of the valved holding chamber with the cap in a closed position.

FIG. 44 is an enlarged, partial cross-sectional view of a latching interface between the first and second housing components.

FIG. 49 is a cross-sectional view of a portion of a valved holding chamber with an alternative backpiece.

FIG. 50 is a cross-sectional view of a portion of a valved holding chamber with an alternative backpiece.

FIG. 60 shows an alternative embodiment of an anti-rattle feature.

FIG. 61 shows an alternative embodiment of an anti-rattle feature.

FIG. 62 shows an alternative embodiment of an anti-rattle feature.

DETAILED DESCRIPTION OF THE DRAWINGS AND THE PRESENTLY PREFERRED EMBODIMENTS

Figure 1:
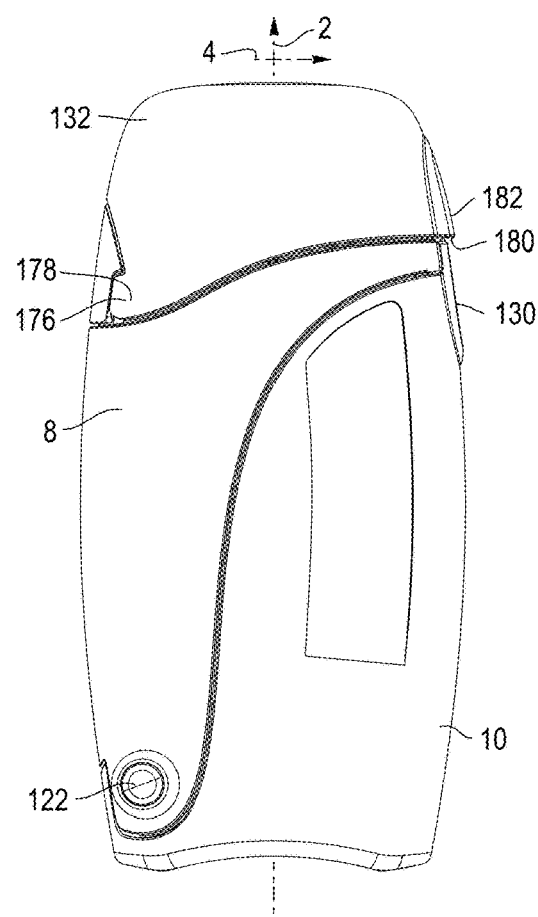
FIG. 1 is side view of one embodiment of a valved holding chamber in a closed, storage configuration with a cap in a closed position.

It should be understood that the term "plurality," as used herein, means two or more. The term "coupled" means connected to or engaged with whether directly or indirectly, for example with an intervening member, and does not require the engagement to be fixed or permanent, although it may be fixed or permanent (or integral), and includes both mechanical and electrical connection. The terms "first," "second," and so on, as used herein are not meant to be assigned to a particular component so designated, but rather are simply referring to such components in the numerical order as addressed, meaning that a component designated as "first" may later be a "second" such component, depending on the order in which it is referred. It should also be understood that designation of "first" and "second" does not necessarily mean that the two components or values so designated are different, meaning for example a first component may be the same as a second component, with each simply being applicable to separate but identical components. The term "longitudinal" refers to a lengthwise direction 2 or axis, and extends along a flow direction of the holding chamber. The term "lateral" refers to a sideways direction 4 or axis that is orthogonal to the longitudinal direction. As used herein, "upstream" and "downstream" refer to the direction of the flow of gases during the inhalation and exhalation sequence of a breathing cycle. As used herein, the terms "exhaust" and "exhalation" are interchangeable.

Holding Chamber

Referring to FIGS. 1-8, a holding chamber 6 includes a first housing component 8 and a second housing component 10. In one embodiment, the first housing component includes a body portion 12 and a user interface portion 14 coupled to the body portion. It should be understood that the body portion and user interface portion may be integrally formed, for example when the holding chamber is configured without an inhalation valve. The body portion has an end wall 16 defining an outlet opening 18, a pair of side walls 20 and a spine wall 22 connecting the side walls, with the side walls and spine wall having a generally U-shaped cross-section and defining a portion of a chamber wall and interior space 24. The end wall 16 is generally dome shaped with a convex outer surface 26 and a concave inner surface 28. A shoulder 30, or sealing ledge, is formed at the interface between the end wall and the chamber wall. A plurality of tabs 32 extend from the end wall.

The outlet opening 18 surrounds a central baffle 34 generally elongated in the lateral direction 4, and which has an elliptical or obround shape in various embodiments. A valve seat 36, having a matching shape, for example elliptical or obround, is defined by a peripheral edge or rib of the baffle extending downstream toward the user interface. A plurality of spokes 38, or connecting members, connect the baffle to the end wall and define the outlet opening 18 therebetween, with the understanding that the phrase "outlet opening" may include a single opening or a plurality of openings. A sealing ledge is defined around the outer periphery of the outlet opening and faces downstream toward the user interface. A longitudinally extending side wall portion 42 extends from the sealing ledge.

The user interface portion 14 has a generally dome shaped end wall 44 that defines a cavity 47 dimensioned to fit over the end wall of the body portion 12. The user interface has an outlet opening 46 aligned with the outlet opening 18 along a longitudinal axis, with the outlet opening being defined by a mouthpiece 50 having a lip portion, which may protrude slightly from the dome shaped wall. The user interface portion has a plurality of openings 52 positioned to engage the tabs on the end wall of the body portion with a snap-fit engagement. It should be understood that the tabs and openings, otherwise referred to as attachment features, may be reversed and positioned on the other of the body portion and user interface, or that the user interface and body portion may be coupled with other fastener systems, friction fit adhesives, and/or combinations thereof.

Figure 29:
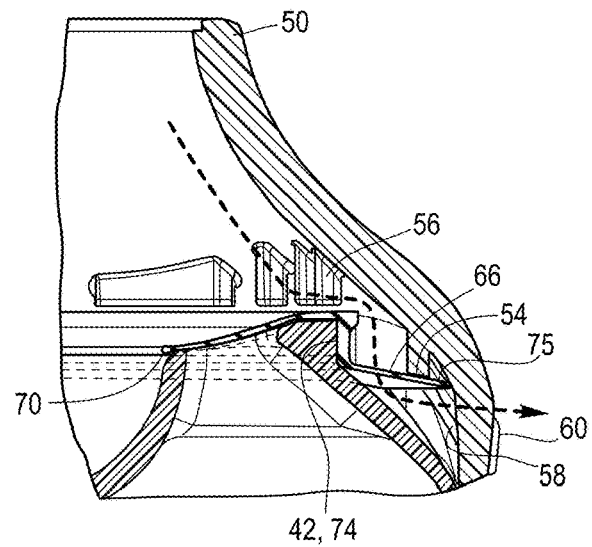
FIG. 29 is a cross-sectional view of a portion of the exhalation valve.
Figure 30:
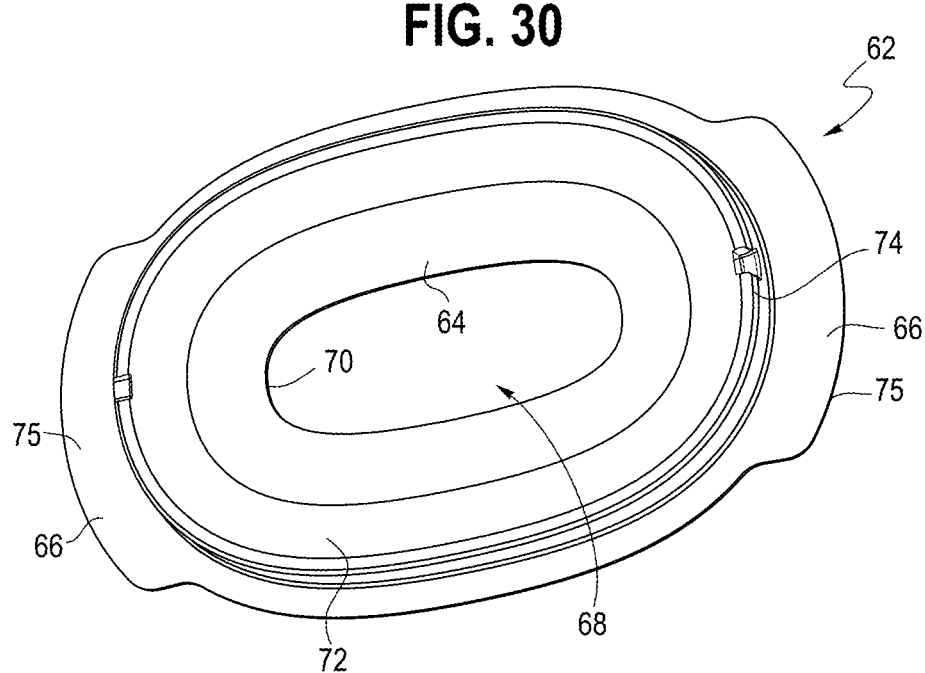
FIG. 30 is a perspective view of the inhalation and exhalation valve.
Figure 40:
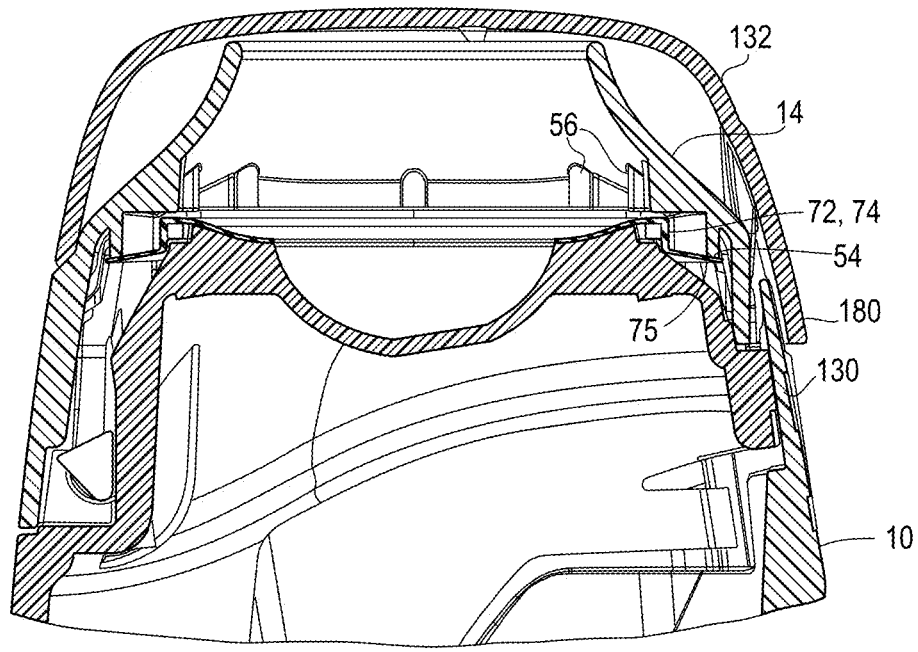
FIG. 40 is an enlarged, partial cross section showing the interface between the cap and first and second housing components, including the user interface.
Figure 41:
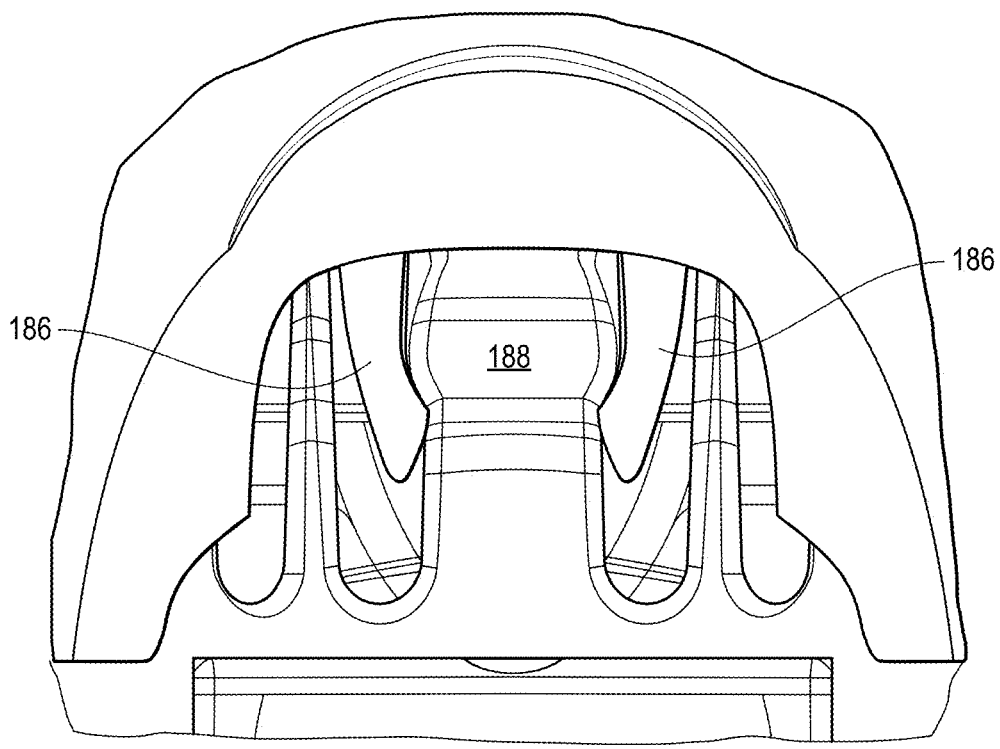
FIG. 41 shows the interface between the user interface and the cap in a closed position.

The user interface portion 14 has a pair of laterally spaced valve seats 54 facing an upstream direction as shown in FIGS. 29 and 40. In addition, a plurality of retaining ribs 56 extend in the upstream direction toward the end wall 16. The retaining ribs 56 overlie the sealing ledge 40 defined around the outer periphery of the outlet opening. As shown in FIGS. 11, 12, 29 and 40, the user interface 14 includes exhalation ports 58 defined by a grill 60 formed in the dome shaped wall downstream of the valve seat, with the ports 58 communicating between the flow channel and the ambient environment. Various aspects of the valve, baffle and user interface are disclosed in U.S. Pat. No. 6,293,279, the entire disclosure of which is hereby incorporated herein by reference.

Referring to FIGS. 17-19, 28-30, and 66, a two-way valve 62 includes an inhalation valve portion 64 and an exhalation valve portion 66. The inhalation valve portion 64 has a central opening 68 shaped to overlie the baffle, with a peripheral edge 70 defining a sealing surface of the inhalation valve that engages the valve seat 36. In one embodiment, the opening 68 has an elliptical or obround shape. The elliptical shape of the valve allows for uniform opening and airflow during inhalation, which results in better performance compared with the traditional valve design using radial symmetry. The valve provides for a functional two-way valve to be included in the portable holding chamber design, minimizing the impact on size. As such, the holding chamber provides good performance to users while maintaining a small size, due to the relative thinness or reduced width, and portability of the case. The shape of the valve also results in a repeatable, uniform opening and flow on inhalation, providing the user with better device performance, while also allowing for the overall device to be made more narrow in a width or depth direction.

Figure 65:
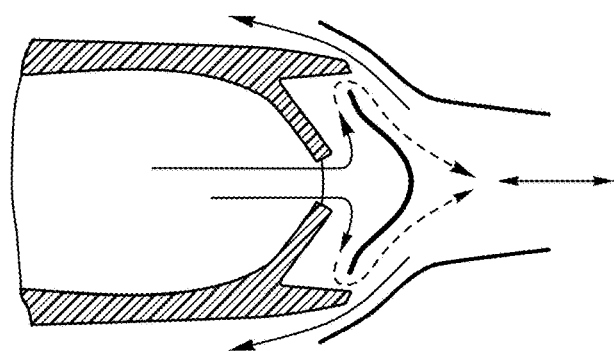
FIG. 65 is a partial cross-sectional view of one embodiment of a valve-less holding chamber.

Alternatively, as shown in FIG. 65, the holding chamber may be configured with carefully considered inhalation and exhalation flow path geometry to prevent disturbing the aerosol inside the chamber. An exhalation path that imparts neither positive nor negative pressure to the volume of the chamber containing the aerosol, however on inhalation aerosol will be drawn out of the holding chamber through the mouthpiece. In this way, the valves may be omitted, with the attendant cost savings, ease of manufacture and assembly, and the attendant failure points and assembly steps.

The valve has a base portion 72 surrounding the inhalation valve portion, with the exhalation valve portions 66 being configured as a pair of laterally spaced flaps extending from the base portion. The flaps have a free edge 75 defining a sealing portion that underlies and engages the valve seats 54 formed on the user interface. The base portion has a longitudinally extending wall that surrounds and engages the wall 42 formed on the end wall 16.

Figure 66:
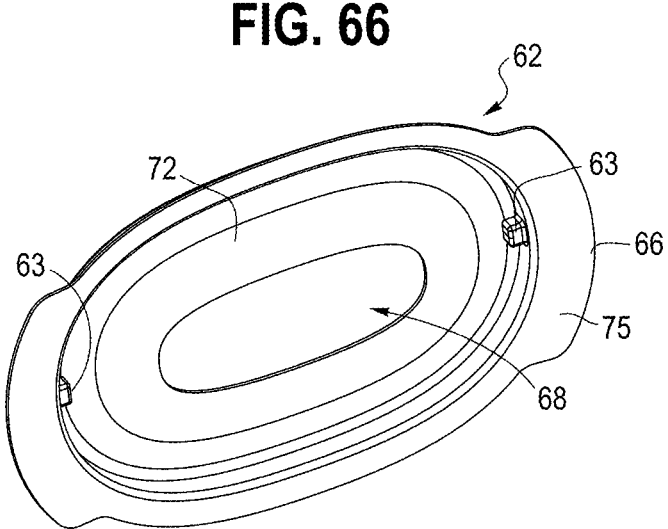
FIG. 66 is a perspective view of the inhalation and exhalation valve.
Figure 67:
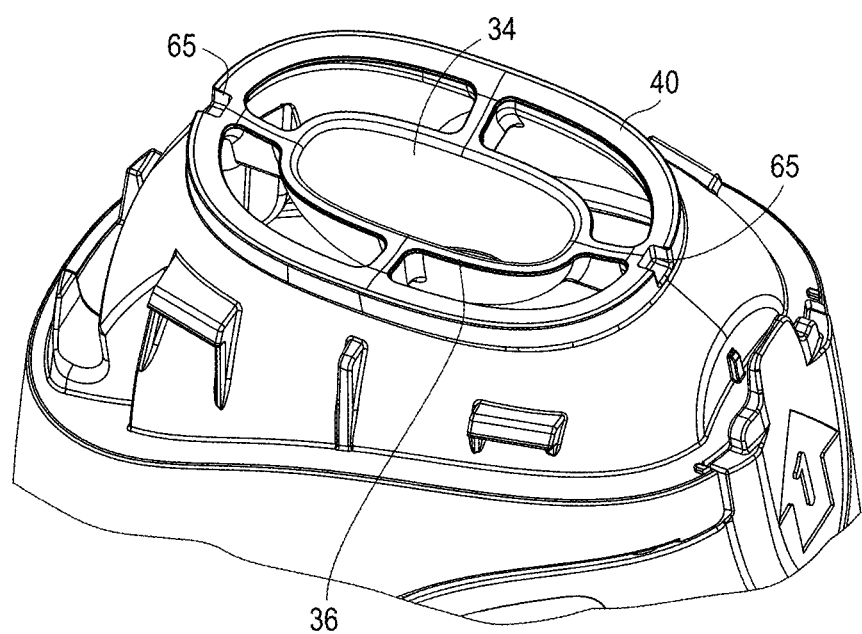
FIG. 67 is a partial perspective view of the body portion.
Figure 68:
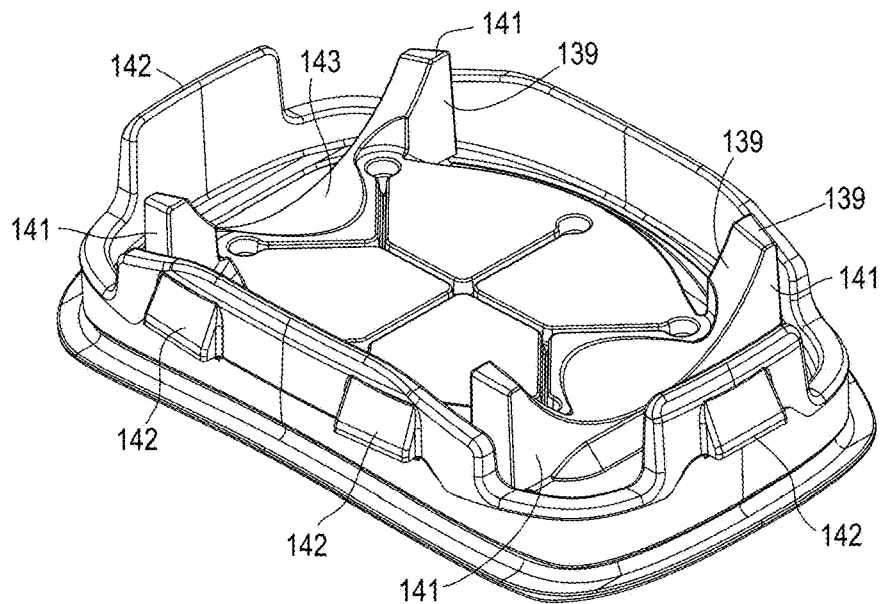
FIG. 68 is a perspective view of one embodiment of a backpiece.

The valve 62 is positioned on the end wall 16, with the base portion 72 engaging the sealing ledge 40 and the wall 74 abutting and engaging the side wall 42, with the interface between the walls 42, 74 locating the valve in the proper orientation and position. The user interface 14 is then coupled to the body portion 12 by way of engagement between the tabs 32 and openings 52, with the valve 62 trapped between the user interface and body portion, the sealing portion 70 of the inhalation valve 64 engaging the inhalation valve seat 36 and the sealing portion of the free edge 75 of the exhalation valve 66 engaging the exhalation valve seat 54. As shown in FIGS. 66 and 67, the valve 62 includes a pair of alignment tabs or ribs 63 positioned on opposite sides of the base portion 72. The ribs 63 are disposed in recesses or openings 65 defined or formed in the outboard side of the sealing ledge 40. It should be understood that the ribs 63 and openings 65 may be reversed, with the opening formed in the valve and the ribs formed on the sealing ledge. Also, the ribs and openings may be positioned anywhere along the base portion, for example at locations 90 degrees relative to those shown in FIGS. 66 and 67, or the valve may include more than two tabs. The location of the ribs shown in FIGS. 66 and 67 provides the greatest distance between the ribs, thereby creating a maximum moment arm resisting rotation. The interface of the ribs 63 and openings 65 ensure that the valve is properly positioned against the sealing ledge 40, and to prevent it from dislodging, or rotating/twisting about a longitudinal "z" axis.

Figure 9A:
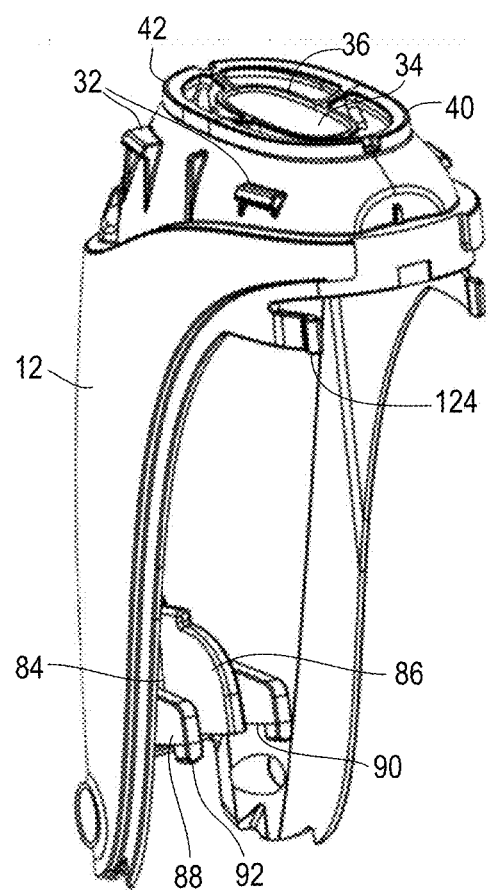
FIGS. 9A and B are a perspective and side view respectively of a first housing component.
Figure 9B:
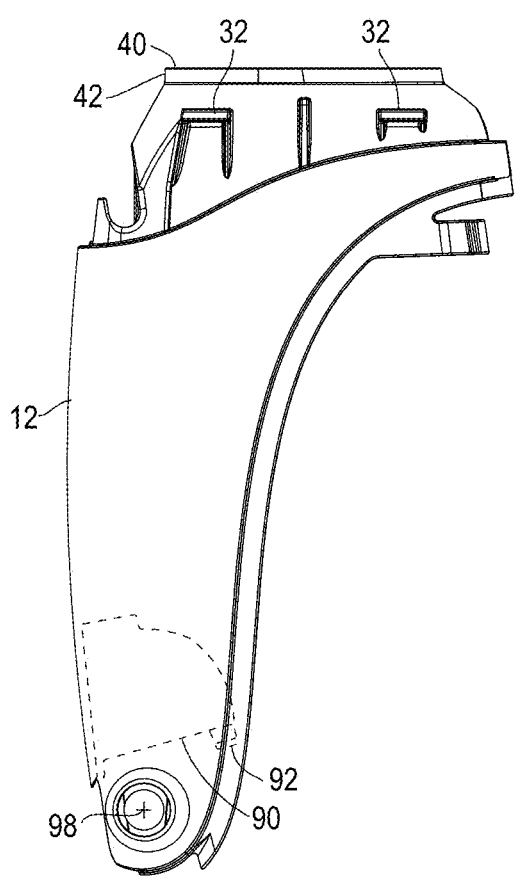
Figure 13:
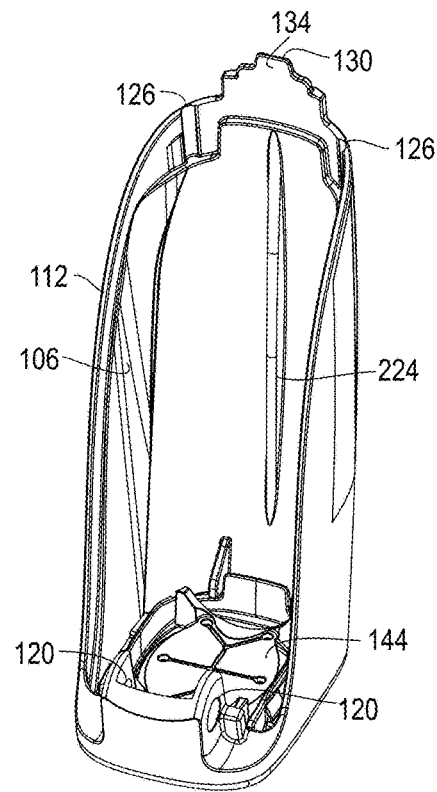
FIG. 13 is a perspective view of a second housing component.
Figure 47:
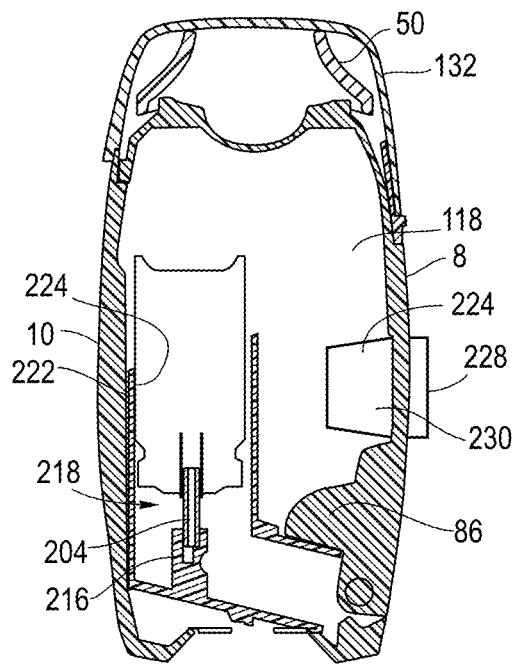
FIG. 47 is a cross-section of the valved holding chamber with a stored MDI take along line 47-47 of FIG. 43.
Figure 48:
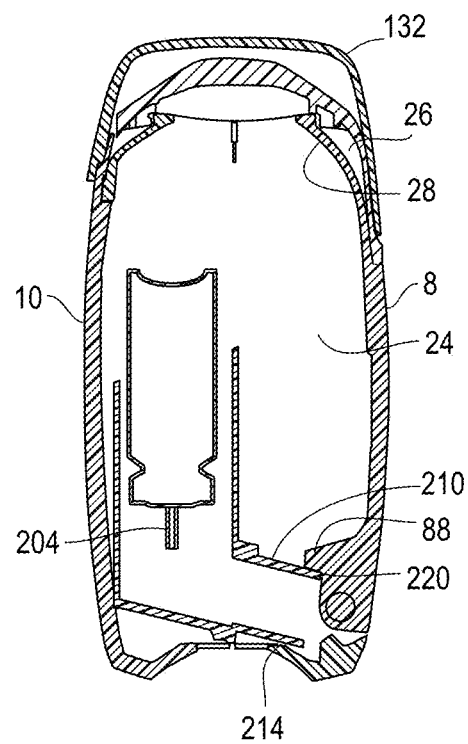
FIG. 48 is a cross-section of the valved holding chamber with a stored MDI take along line 48-48 of FIG. 43.

The chamber wall has a curvilinear edge 76, with an upper concave curvature 78 along the side walls adjacent the user interface and a lower convex curvature 80 adjacent an opposite end, and a transition therebetween. The width of the side walls, and the attendant depth of the interior space 24, decreases along the length of the chamber wall. The end 82 of the chamber wall opposite the end wall includes an engagement member 84, which may be integrally formed with the body portion of the first housing component as shown in FIGS. 47 and 48, or separately formed and coupled to the first housing component, for example with a snap fit as shown in FIGS. 9A and B, 15, 71, 72 and 74A and B. The engagement member 84 includes a plurality of laterally spaced fingers or ribs 86, 88, which extend laterally from the spine wall 22 into the interior space, and beyond the edge 76 of the side walls in one embodiment. In one embodiment, the engagement member includes a centrally located primary rib 86 or finger and a pair of auxiliary ribs 88 or fingers spaced apart on each side of the primary rib or finger. The primary rib or finger extends laterally into the interior space a greater distance than the auxiliary ribs or fingers. Each rib or finger has an engagement surface 90, 92 facing upstream and a bearing surface. The engagement member, or the end of the body portion is configured with a hinge component, which may include one or more lugs having axially aligned openings that define a pivot axis 98.

Figure 71:
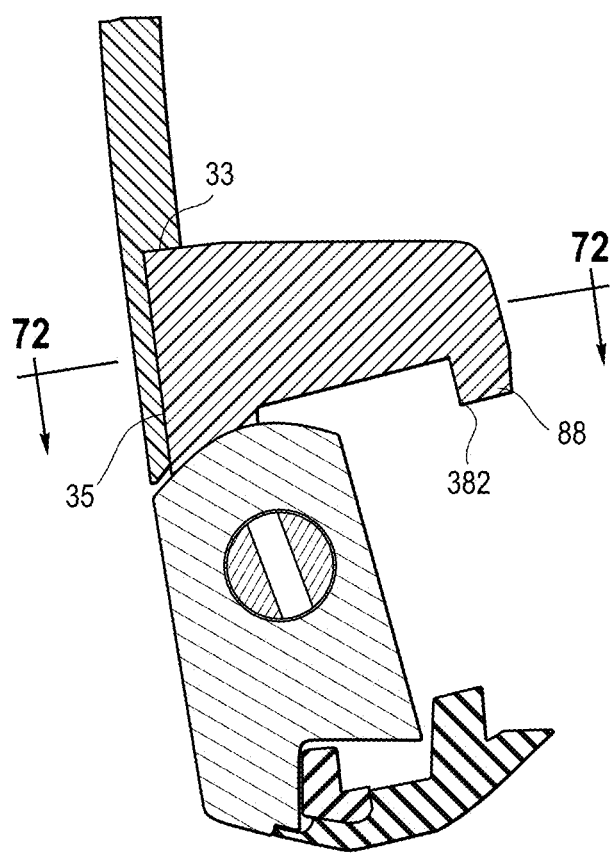
FIG. 71 is a partial cross-sectional view of an anti-rattle component secured to a holding chamber.
Figure 72:
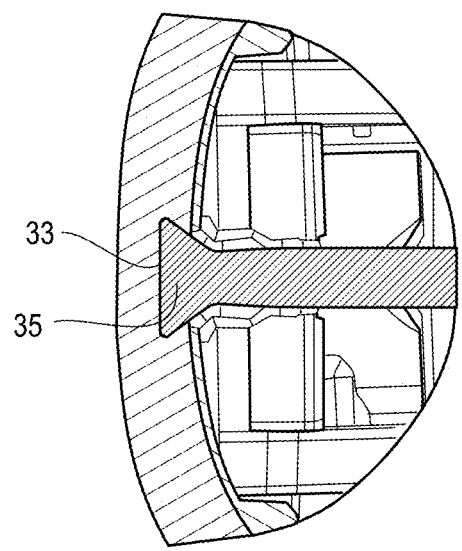
FIG. 72 is a cross-sectional view of the anti-rattle component secured to a holding chamber taken along line 72-72 of FIG. 71.
Figure 74A:
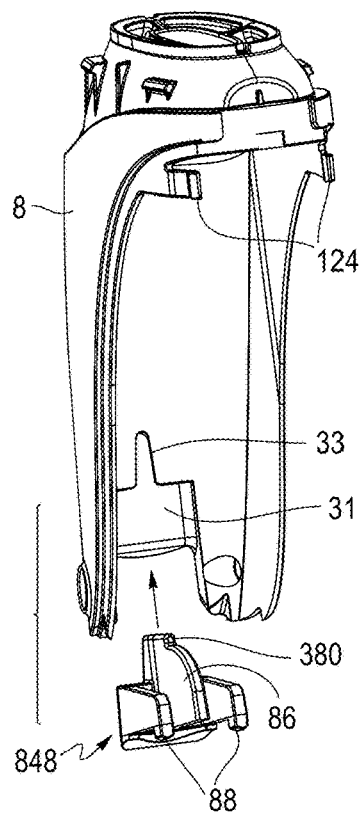
FIGS. 74A and B are front perspective views of an anti-rattle component applied to a holding chamber.
Figure 74B:
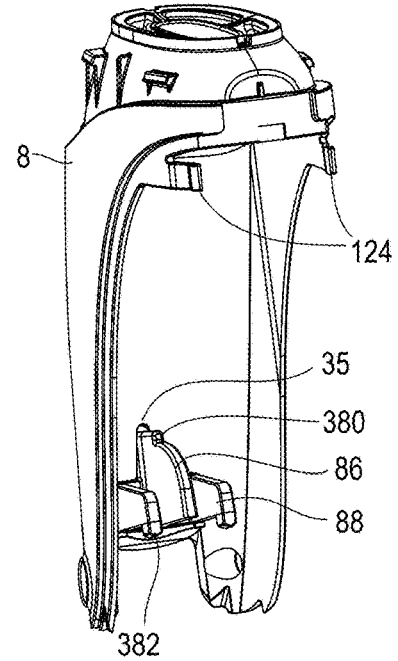

Referring to FIGS. 71, 72 and 74A and B, the housing component 10 has a recess 31 shaped to receive a back wall of the engagement member, and a slot 33 extending longitudinally from an edge of the recess. The slot 33 defines a track, and has a dove-tail shape in one embodiment. The engagement member 84 in turn includes a rib 35, which may be an opposite side of the primary rib, with an edge having a corresponding dove-tail shape that may be slidably engaged with the track to secure the engagement member to the housing component with a press fit. After the housing component 12 is secured to the housing component 10, for example with a hinge pin, the engagement member is locked in place and cannot be removed. The ribs 86, 88, individually or in combination, may engage the mouthpiece of the MDI, for example at spaced apart locations. Alternatively, the ribs may be disposed in the interior of the mouthpiece, with a shoulder or engagement surface on the central rib 86 engaging an end of the mouthpiece of the MDI.

Figure 14A:
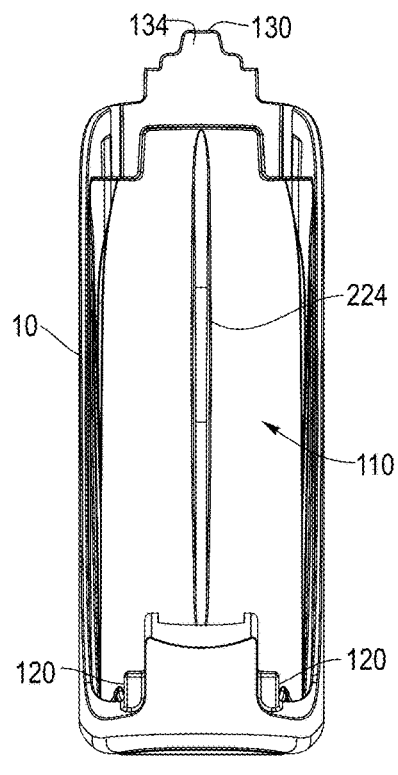
FIGS. 14A and B are end and side views respectively of the second housing component.
Figure 14B:
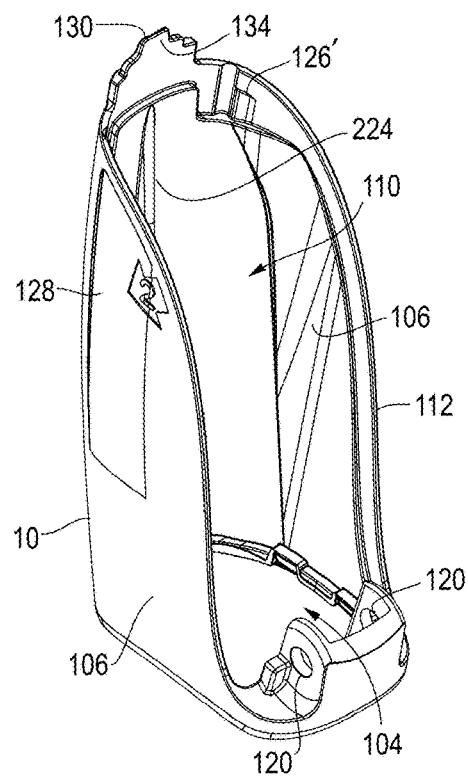
Figure 15:
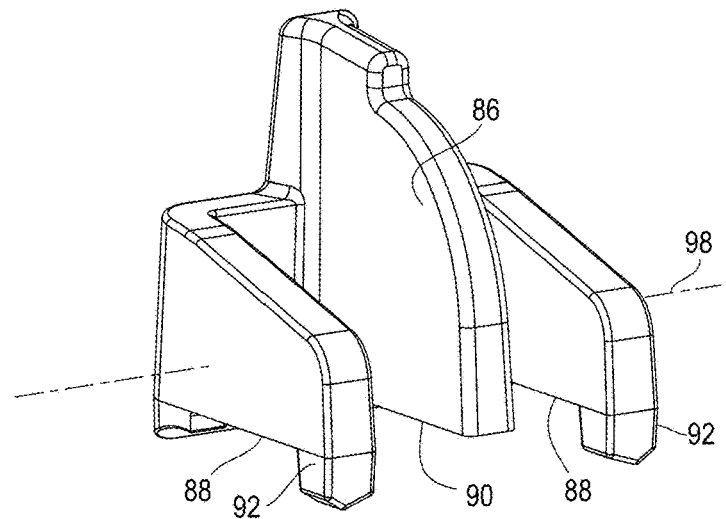
FIG. 15 is a perspective view of an MDI engagement component.
Figure 16:
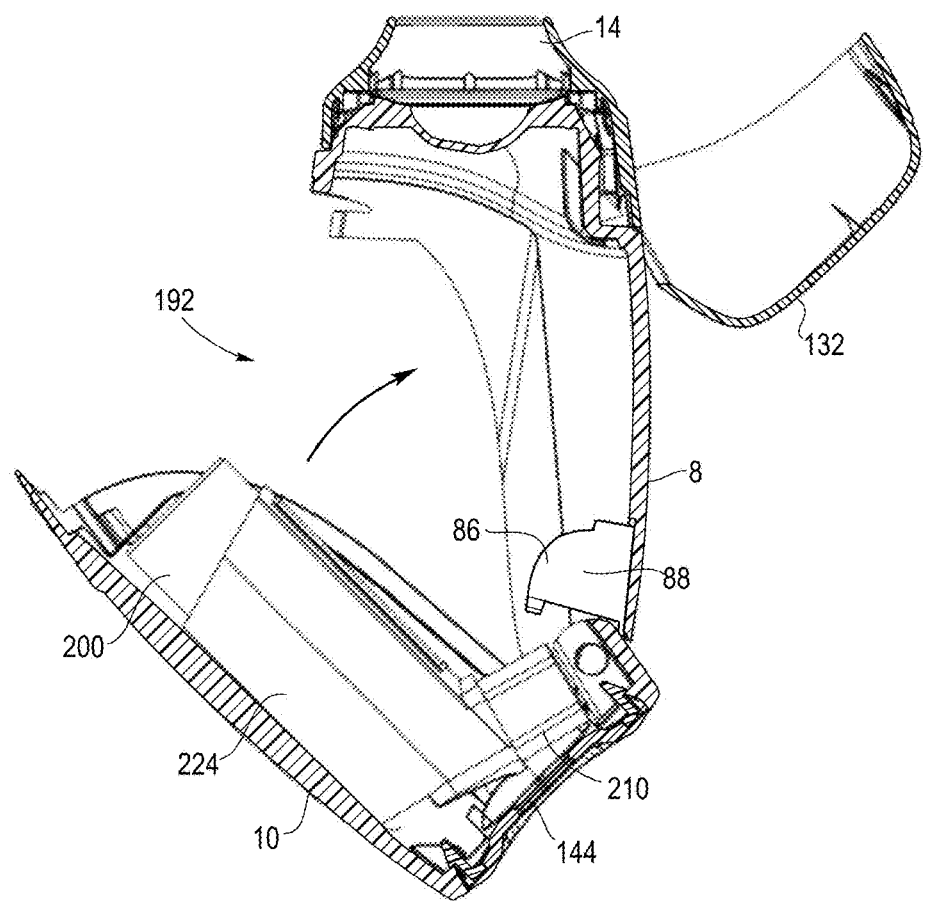
FIG. 16 is a side of a valved holding chamber in an open configuration and the cap in an open position, with a metered dose inhaler disposed in the interior space of the holding chamber.

Referring to FIGS. 14A and B and 17-19, the second housing component 10 includes a body portion 100 having an end wall 102 defining an inlet opening 104, a pair of side walls 106 and a spine wall 108 connecting the side walls, with the side walls and spine wall having a generally U-shaped cross-section and defining a portion of a chamber wall and interior space 110. The chamber wall, and each side wall in particular, has a curvilinear edge 112, with a lower concave curvature 114 adjacent the end wall and an upper convex curvature 116 along the side walls adjacent the user interface and. The width of the side walls 106, and the attendant depth of the interior space 110, decreases along the length of the chamber wall. The edges 76, 112 of the chamber walls are shaped to mate. It is desirable to minimize the ingress for lint or other contaminants into the overall interior space or chamber 118 (see FIG. 47), defined by the combination of the interior spaces 24, 110 of each housing component in a closed configuration, during transport or other non-use, since foreign substance finding a way inside the interior chamber 118 of the VHC may potentially be inhaled by the user. Accordingly, the first and second housing components 8, 10, which make up the body of the VHC, may be sealed along any interfaces where the components meet and form a seam. This interface should create a seal and prevent any dust or debris from entering the chamber 118 when the first and second housing components are in the closed configuration. In one embodiment, a bead of flexible material may be overmolded on the component interface, or edges 76, 112. The soft material will compress and create a seal. The interface between the two parts may alternatively be formed as a tongue and groove joint between the edges 76, 112 to provide a seal against the outside. Alternatively, the interface may have an O-ring disposed between or along one of the edges 76, 112 of matching shape and size to provide a seal. In another alternative embodiment, the interface between the housing components, and edges 76, 112 in particular, is provided with a half lap joint to provide a seal against the outside. Combinations of these interfaces may also be suitable, for example with a lap joint and seal being provided. The seal, such as a rubber or silicone bead, may be disposed along one of the edges such that the seal engages the other of the edges.

The side walls are configured with a hinge component 120, which may include axially aligned openings that define the pivot axis 98 when aligned with the opening of hinge component 96. The openings of the first and second housing components are aligned, with a hinge pin 122 extending through the openings of the hinge components 96, 120 and pivotally connecting the first and second housing components. It should be understood that one or both of the first and second housing components may be configured with an integrally formed hinge pin that engages the other of the housing components, or the components may be coupled with a living hinge.

Referring to FIG. 44, the first and second housing components 8, 10 are releasably connected with a latch or detent, configured with a pair of resilient tabs or fingers 124 extending from the first housing component engaging corresponding notches 126 formed on the second housing component. When the first and second housing components are pulled apart with sufficient force, the fingers flex 124 inwardly and are released from the notches 126, allowing the housing components to separate. It should be understood that the fingers and notches may be arranged on the other of the first and second housing components.

Grips 128 are provide on one or both side walls 106 of the second housing component to aid in pinching and applying a pull force to the housing components. The grips 128 also provide a visual cue to the user about where to grasp the components. The grips are formed as a subtle recessed area which is blended seamlessly into the outer surface of the device. The grips may alternatively be provided on the first housing component, or on both housing components. The grips 128 may be textured, or includes a soft material, or be formed as any shape or addition to the part which will aid the user in gripping the device with enough force to overcome the body latch 124/126 and open the case.

Figure 45:
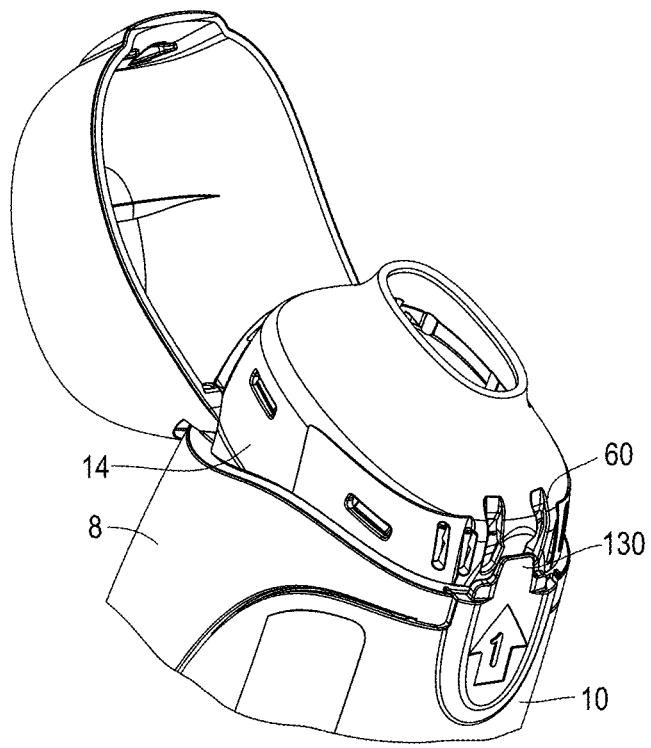
FIG. 45 is a partial, perspective view of the valved holding chamber with the cap in an open position.
Figure 46:
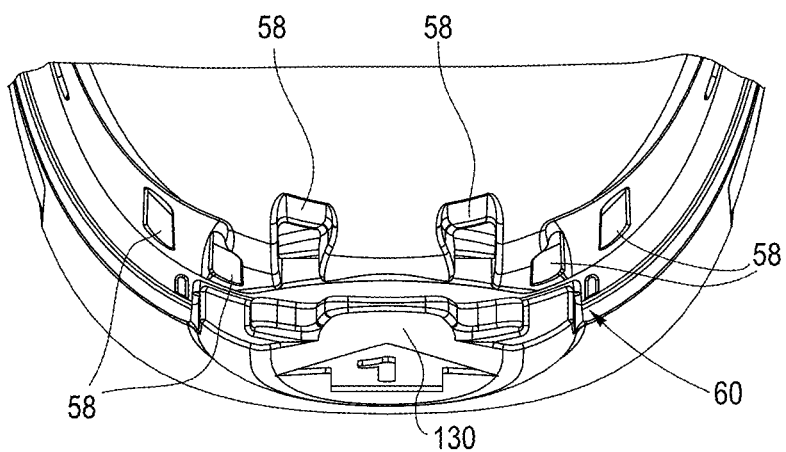
FIG. 46 is a partial, top view of the valved holding chamber with the cap in an open position.

As an alternative, once the cap is in the open position, a tab 130 is revealed and extends upwardly from the spine wall 108, or other part of the second housing component as shown in FIGS. 45 and 46. The tab 130 is engaged by the cap 132 and prevents the components from opening when the cap is in a closed position as further explained below. A user may pull on the tab 130 with a finger or fingernail to open the body. The tab 130 is designed with a section cut out 134 to ensure the design is simple and comfortable to use. Conversely, the cap 132 may include a feature, such as a tab 136 to aid in forcing the cap open, overcoming a latch feature between the cap and user interface. The tab 136 may have a slight overhang to push against on the cap, allowing the user to produce force in the correct direction to open the cap.

Figure 73:
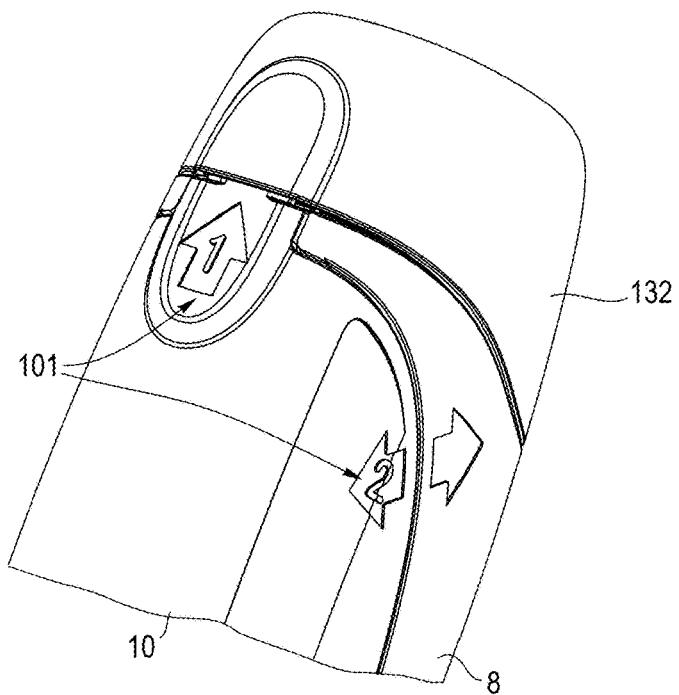
FIG. 73 is a partial perspective view of a holding chamber with instructional indicia applied thereto.

Referring to FIG. 73, instructional indicia 101, which may include alpha-numerical characters, such as numbers "1" and "2", as well as directional indicia such as arrows, provide instructional information, or visual cues, to the user about the sequence of how to open and use the device. The instructional indicia may be moulded into the plastic, or be applied with adhesive. For example, a number 1 with a first arrow provides indicia to the user that the cap must first be opened and pushed in a particular direction of the arrow. A number 2 with a pair of second directional arrows notifies the user that the second step is to open the two housing components by moving the components in opposite directions.

As noted, the first and second housing components, collectively referred to as a body, open along a split line defined by the edges 76, 112, which cuts diagonally across the middle of the device crossing the longitudinal axis between the user interface outlet and the inlet opening. The split line is a stylized curve, such that when inserted into the interior space of the body in a stored configuration, the MDI is cradled by one side of the chamber. Of the two housing components making up the chamber body, one of the housing components (e.g, the first housing component 8), or a portion thereof defining a viewing window, is preferably "see-through," meaning it is clear, semi-transparent, transparent or translucent while the other (e.g., the second housing component 10) is opaque. This creates a unique visual impression, accentuated by the curved profile of the line splitting the two housing components. The "see-through" component or window allows users to confirm visually that the medicament delivery device, such as an MDI, is inside the case at any given time without opening the case.

The device is intended to be carried with the user "on the go," and as such must be comfortable and unobtrusive. As such, the cross-sectional shape of the device should be no thicker than necessary to fit an MDI. A smooth outer surface ensures that there are no sharp edges, hinges or fasteners to catch on a pocket or poke into the user.

Referring to FIGS. 20-27, 68 and 69, a backpiece 138 includes a carrier 140, configured as a ring. The carrier 140 has a plurality of tabs 142 that engage the periphery of the inlet opening 104, or an interior catch portion 105, in the end wall 102, providing for a snap-fit connection. The carrier may also be engaged with the end wall, or the chamber wall, with a friction fit, fasteners, adhesives, and the like. A flexible membrane 144 is secured to the carrier, for example by overmolding. The membrane has a border portion 146 secured to the carrier. The border portion defines an end wall 150 and a side wall 152, with a central portion 148 coupled to the side wall 152 and extending across the inlet opening. The membrane side walls and central portion are bowl shaped, with the central portion spaced apart from the end wall in a downstream direction. In this way, the surface is offset inward from the interior surface of the end wall, with the side wall defining a channel or cavity 155 leading to flexible sections or flaps to improve the retention force when an MDI is inserted. The membrane 144 is chemically bonded to the carrier 140, which in turn is engage with the end wall of the second housing component across the inlet opening, for example with a snap fit.

The central portion 148 includes a plurality of flexible sections 154, 160 separated by a plurality of slits 156 defining free edges 162 of the flexible sections.

Figure 26A:
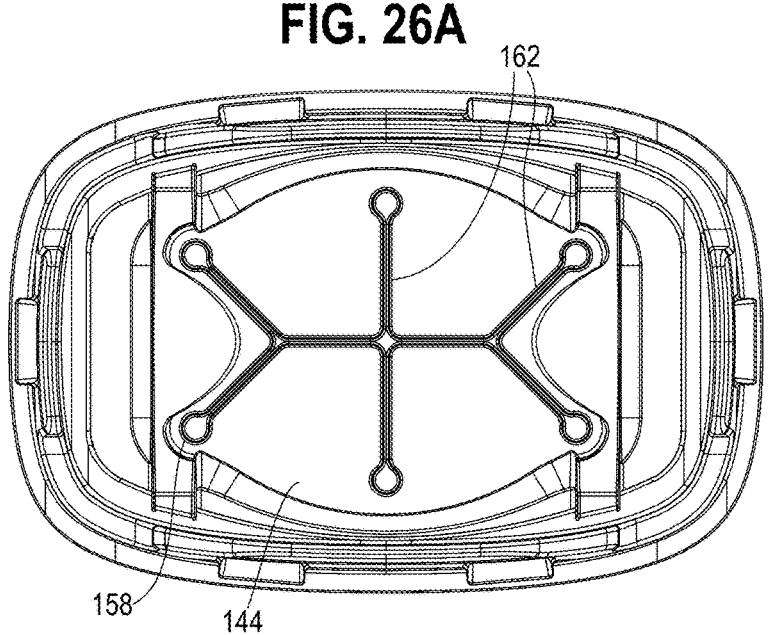
FIGS. 26A and B are interior views of the backpiece in closed and open configurations respectively.
Figure 26B:
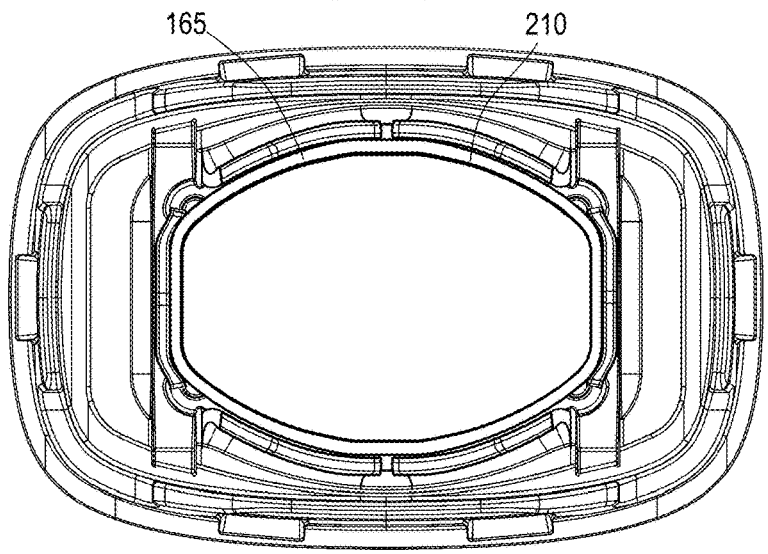
Figure 27:
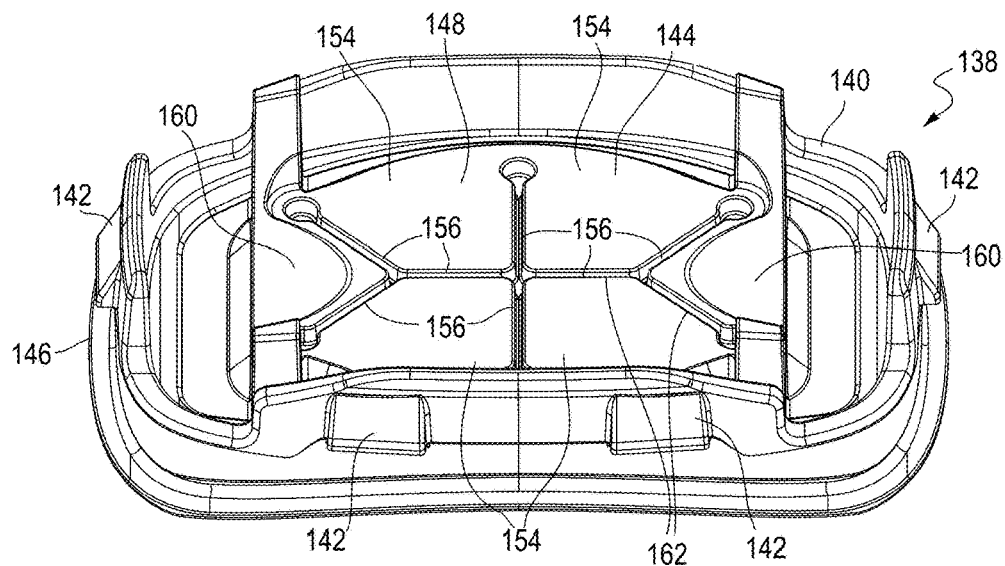
FIG. 27 is an interior perspective view of the backpiece.
Figure 28:
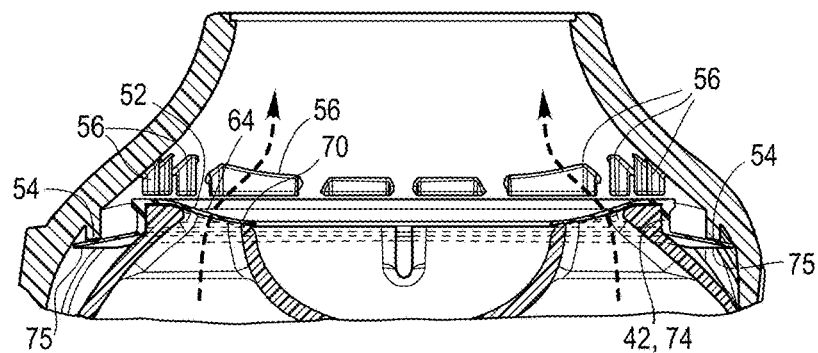
FIG. 28 is a cross-sectional view of the user interface showing the inhalation and exhalation valve.

The flexible sections are moveable relative to each other from a closed configuration, wherein the free edges 162 of adjacent flexible sections are positioned proximate each other as shown in FIG. 26A, and an open configuration, wherein the flexible sections are deformed to define an inlet opening 164 as shown in FIG. 26B. The slits 156, including end relief openings 158, define the only opening through the flexible membrane in the closed configuration. In one embodiment, the plurality of flexible sections includes at least four flexible sections 154, and in a preferred embodiment, incudes six flexible sections, with four central flexible sections and two end flexible sections. The end flexible sections 160 are generally triangular with a pair of free edges 162 and a bounded edge 164 connecting the flexible section to the side wall and defining a living hinge. The central flexible sections 154 are generally quadrilateral with three free edges 152 and a bounded edge 164 connecting the flexible section of the side wall and defining a free edge. Each of the central flexible sections has an innermost free edge, with the free edges running parallel to each other, with opposing free edges abutting each other. The slit formed between the opposing free edges defines an axis 166 that intersects the apex 168 of the end flexible sections 160. The slits 162 between the four central flexible sections 154 define or have a cross, "T" or "X" shaped opening. The free edges 162 of each of the flexible sections are linear in one embodiment, although it should be understood that they may be non-linear, e.g., curved or curvilinear. The free edges 162, and apexes 168, of the two end flexible sections are spaced apart from each other and do not intersect when the flexible sections are in the closed configuration.

Figure 20:
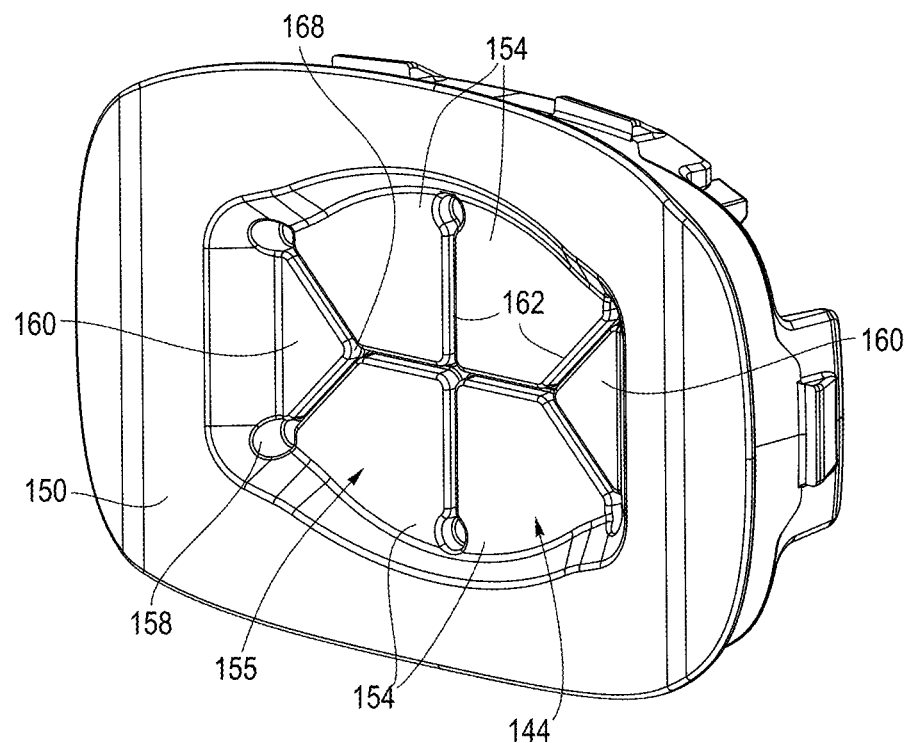
FIG. 20 is an outer, perspective view of a sealable backpiece for a valved holding chamber.
Figure 21:
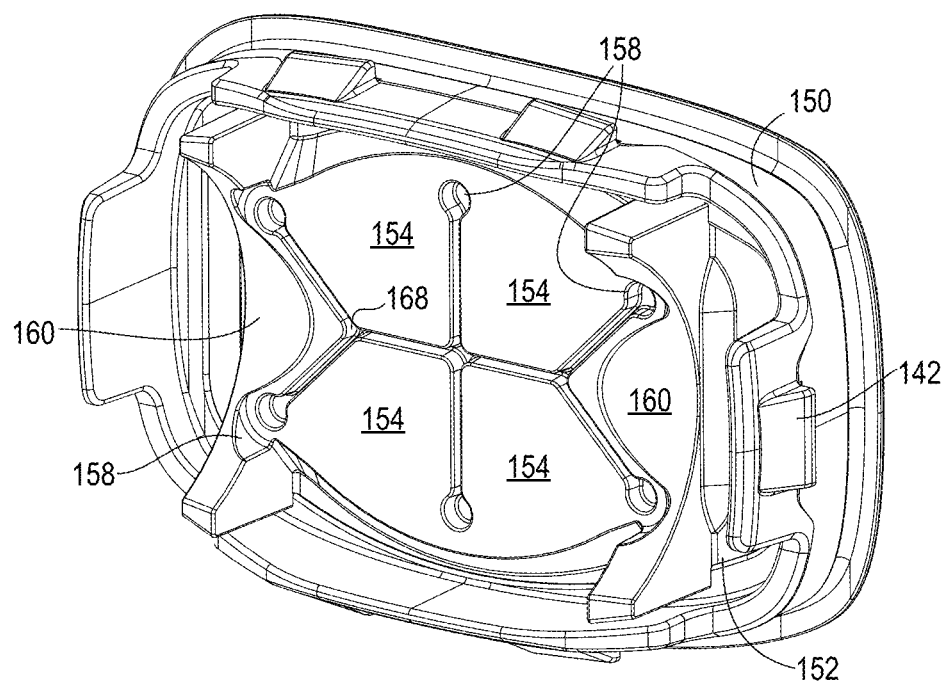
FIG. 21 is an interior, perspective view of the sealable backpiece.
Figure 22:
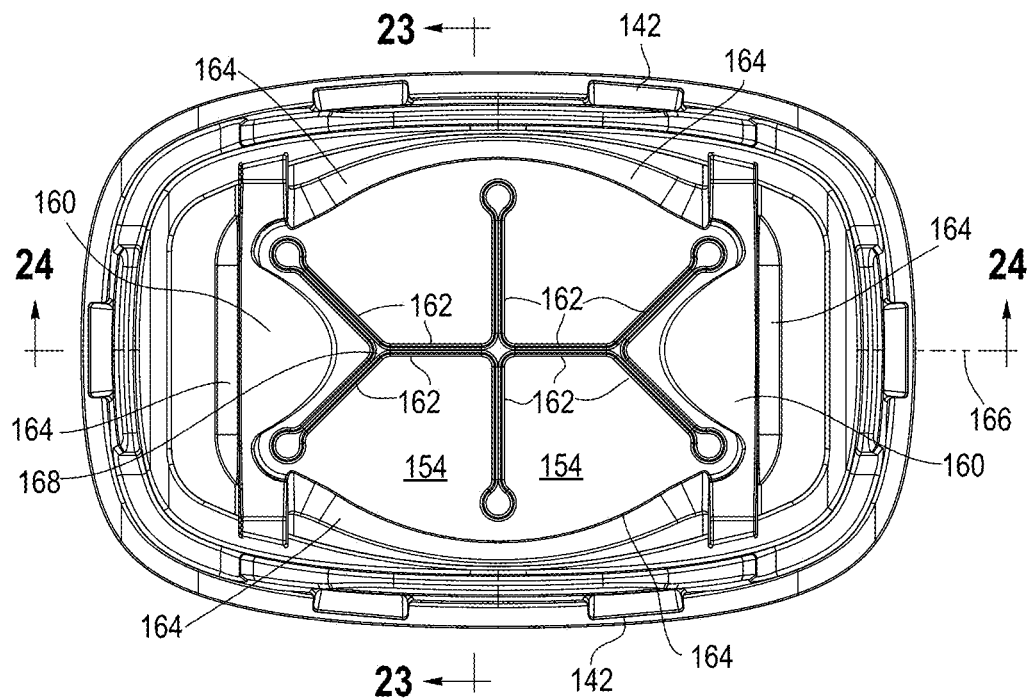
FIG. 22 is a front view of the sealable backpiece.
Figure 23:
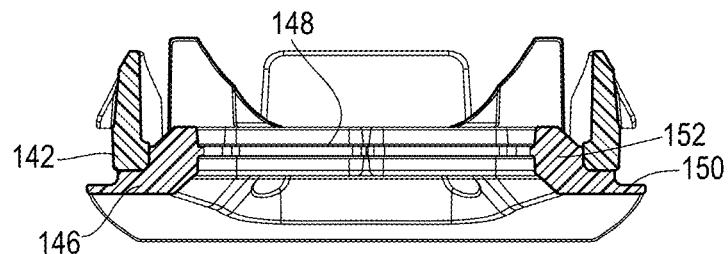
FIG. 23 is a cross-sectional view of the backpiece taken along line 23-23 of FIG. 22.
Figure 24:
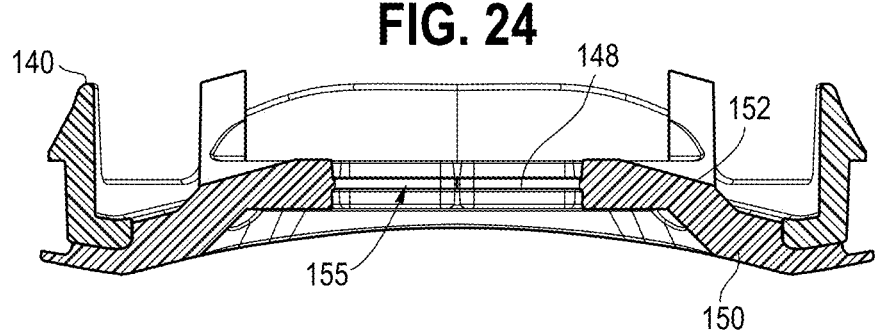
FIG. 24 is a cross-sectional view of the backpiece taken along line 24-24 of FIG. 22.
Figure 25:
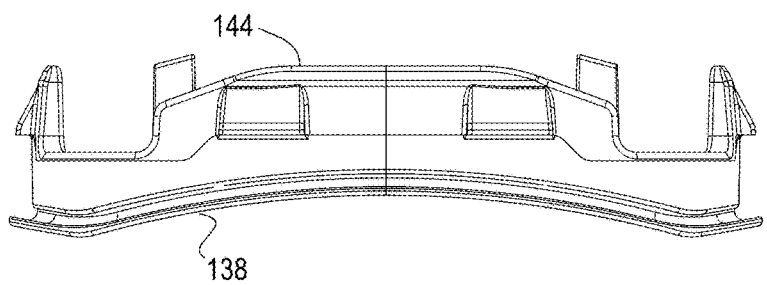
FIG. 25 is a side view of the backpiece shown in FIG. 22.

The inlet opening 165 defined by the flexible sections in the open configuration defines a first area A1. The slits define a second area A2, with A2<A1. Relief openings 158 are positioned at a terminal end of the slits 156 and define in part the slits. The relief openings 158 have a width, for example a diameter if circular, that is greater than the width of the slits 156 with which they terminate. The relief openings 158 reduce the stress concentration and help prevent the slit from propagating (e.g., by tearing) into the border portion while also promoting the flexibility of the flexible sections. The relief opening may be positioned in, or extend into the side wall of the border portion as shown in FIG. 20. The relief openings, configured in one embodiment as round cutouts, reduce tearing in the part and lower the insertion and removal forces for different MDI styles. These features together with the channel ensure the MDI will remain coupled to the device when in use, while the user can comfortably insert and remove the MDI without excessive force.

Figure 69:
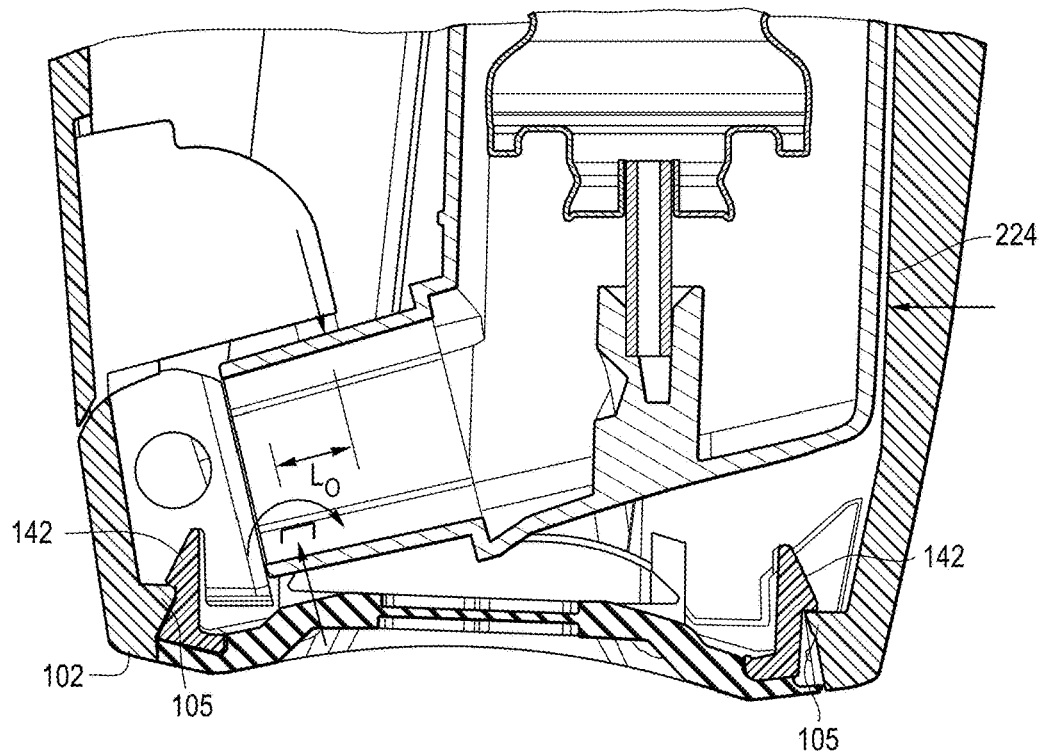
FIG. 69 is a partial interview view of a pressurized metered dose inhaler disposed in a holding chamber.

In one embodiment, the backpiece 138 includes a plurality of supports 139 extending longitudinally from the membrane 144 or carrier. The supports are configured with a pair of spaced apart side extensions or posts 141, with a curved support surface extending therebetween and defined in part by the posts. The support surface is shaped to engage a mouthpiece portion of the pressurized metered dose inhaler, as shown in FIG. 69. The engagement location is offset a distance Lo from the location where the rib 86 engages an opposite surface of the mouthpiece portion, such that the supports 139 and rib 86 apply a moment force to the mouthpiece, and pressurized metered dose inhaler, and thereby rotates the pressurized metered dose inhaler against a rib 224, as further explained below. In this way, the pressurized metered dose inhaler is held securely in the holding chamber and prevented from rattling around therein.

Figure 2:
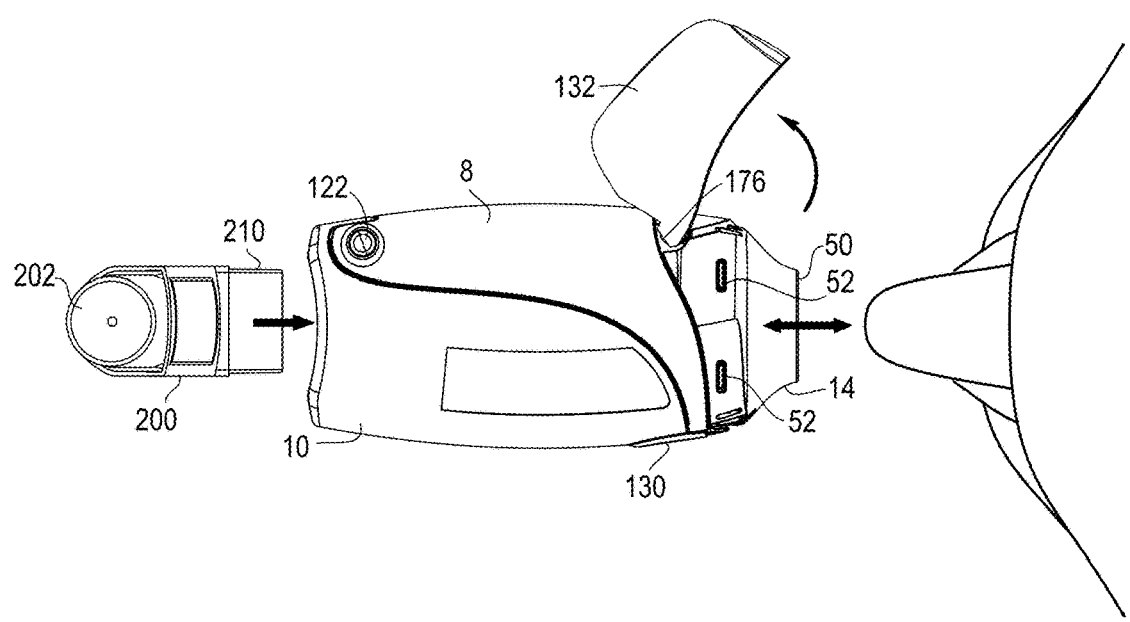
FIG. 2 is a side view of the valved holding chamber in a closed configuration with a cap in an open position.
Figure 3:
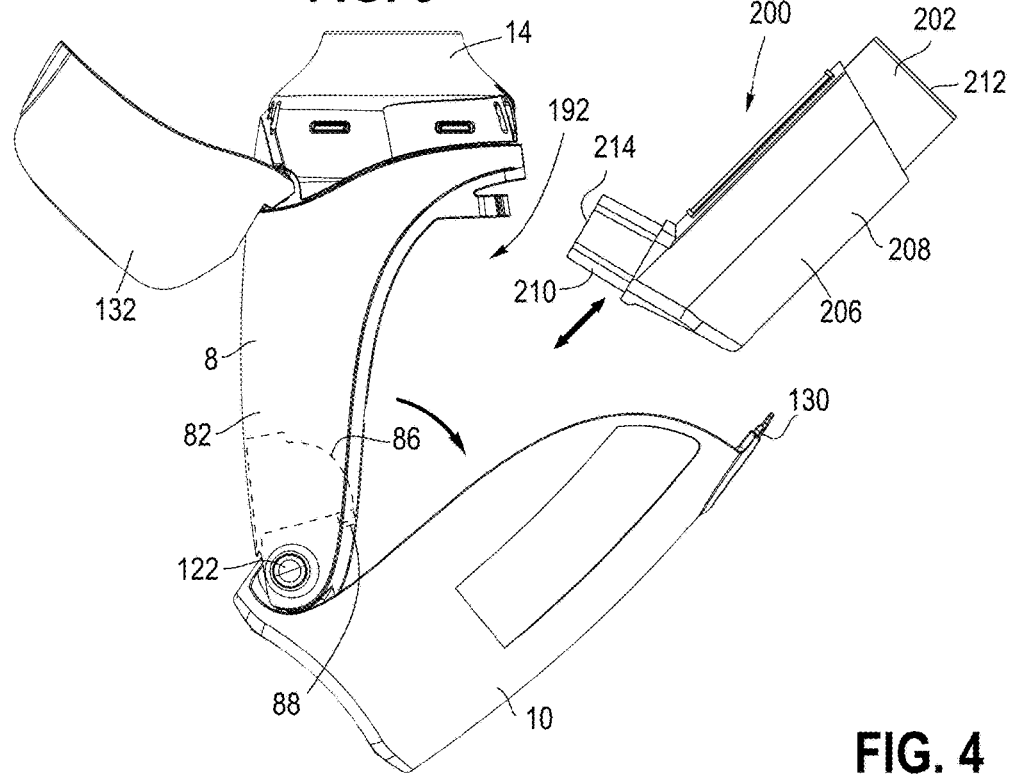
FIG. 3 is a side view of the valved holding chamber in an open configuration.
Figure 4:
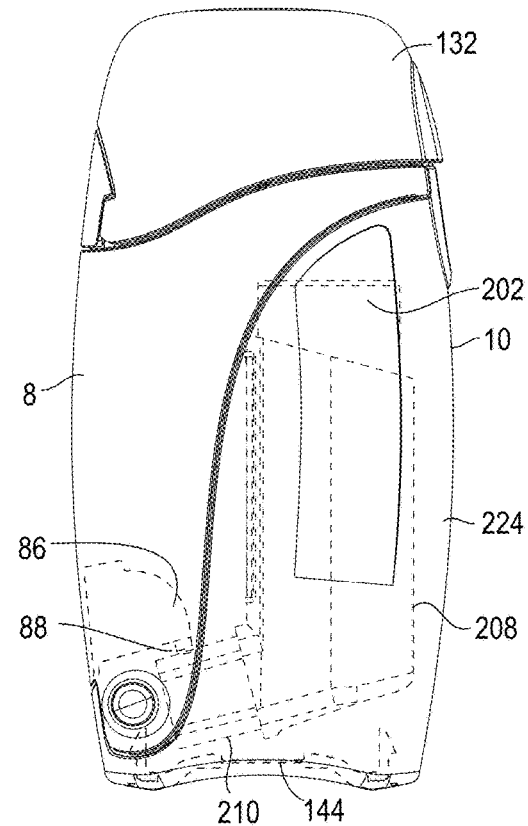
FIG. 4 is a side view of the valved holding chamber in a closed, storage configuration with the cap in a closed position and a metered dose inhaler disposed in the interior of the valved holding chamber.
Figure 5:
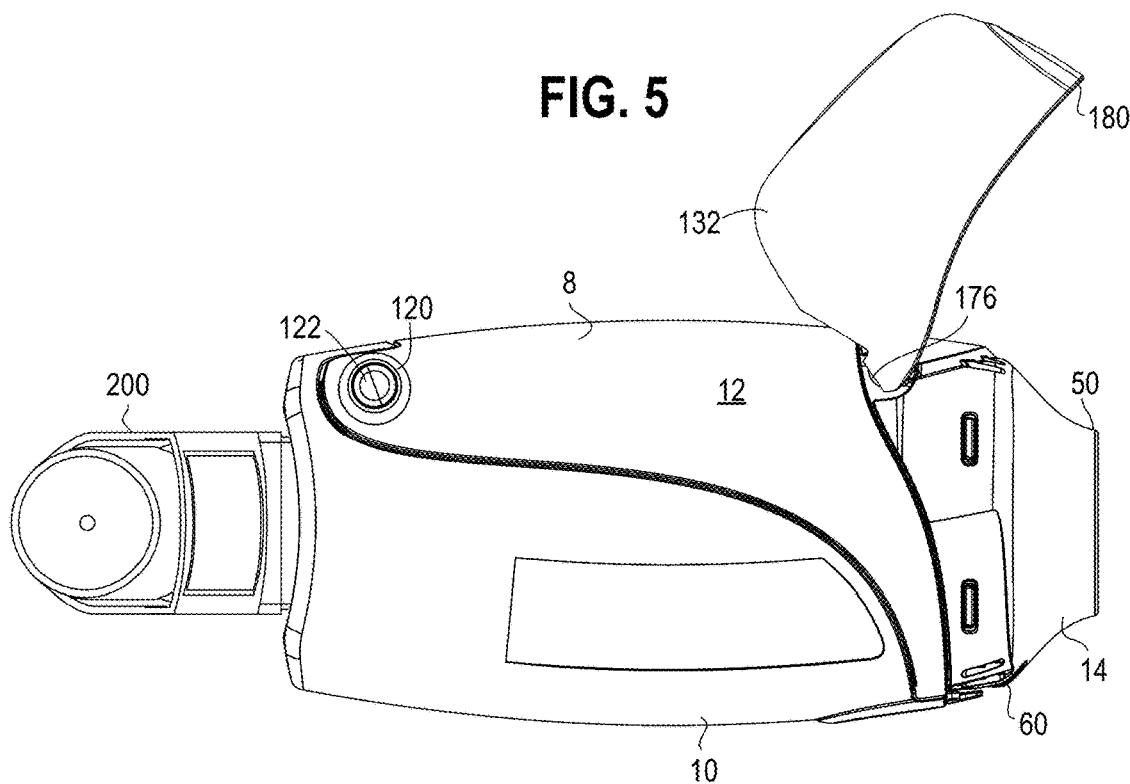
FIG. 5 is a side view of the valved holding chamber in a closed, use configuration with a metered dose inhaler coupled to the inlet opening thereof.
Figure 6:
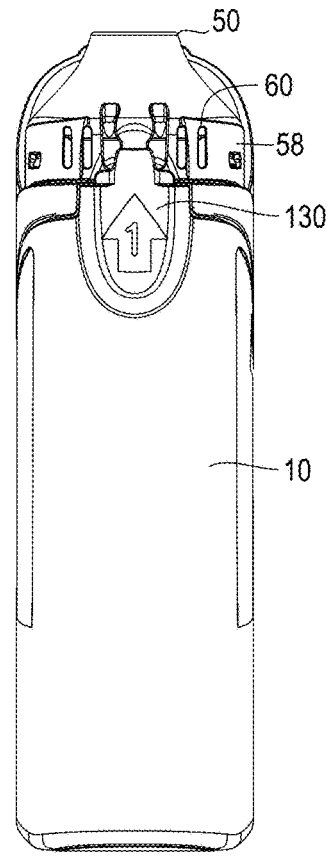
FIG. 6 is an end view of the valved holding chamber in a closed, storage configuration with the cap in an open position.
Figure 7:
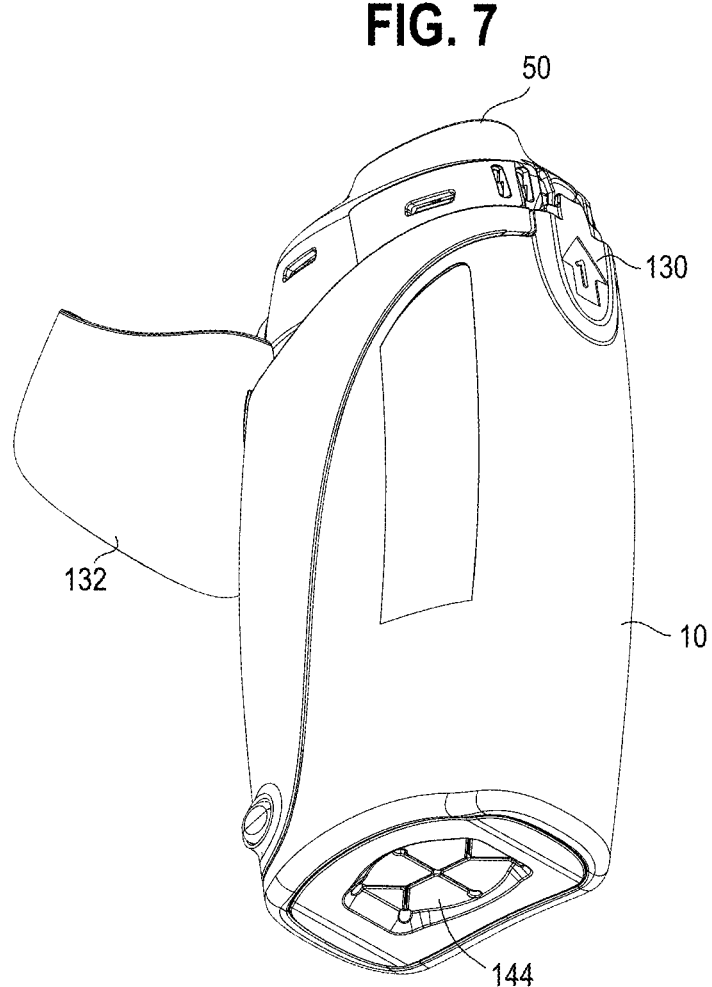
FIG. 7 is a bottom, perspective view of the valved holding chamber in a closed, storage configuration with the cap in an open position. is an end view of the valved holding chamber in a closed, storage configuration with the cap in an open position.
Figure 8:
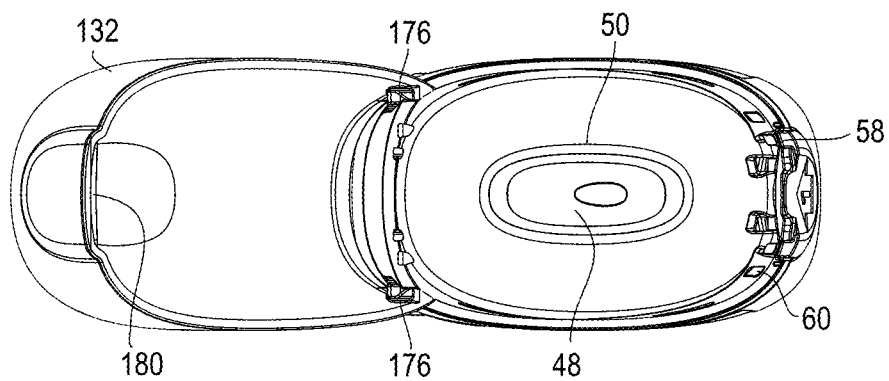
FIG. 8 is a top view of the valved holding chamber in a closed, storage configuration with the cap in an open position.

The inlet opening 165 and the outlet opening 48 of the mouthpiece are substantially aligned along the longitudinal axis 2 when the first and second housing components are in the closed configuration as shown in FIGS. 1 and 2, with the inlet opening and outlet openings being orthogonal to the longitudinal axis. Air, and medicament, follows a flow path during inhalation through the inlet opening into the interior chamber, through the outlet opening as the inhalation valve opens, and through the mouthpiece outlet to the user's airway. During exhalation, the flow path is through the user interface and out the exhalation opening past the exhalation valve.

Referring to FIGS. 1-3, 10-12, 16-18, 41-43, 47 and 48, the cap 132 is moveably connected to the user interface portion 14 of the first housing component. Alternatively, the cap may be moveably connected to the second housing component. The cap has an end wall 169 and side walls 170 that define a cavity 172, which receives the mouthpiece 50 of the user interface portion when the cap is in a closed position. In one embodiment, one or both of the side walls 170 is pivotally connected to the user interface portion about one or more pivot axes 166. The side wall has a concave cutout 174, with a pair of hinge components 176 disposed along the bottom edge. The hinge components are configured as lugs in one embodiment, with the lugs toed inwardly, such that they are not parallel to each other. The user interface includes a pair of pivot pins 178 that are aligned with the hinge components. The configuration of the hinges 176, 178 provides for the outer surface of the user interface portion and the cap side wall to be flush, with a convex curvature. The cap end wall has curved edges on all sides transitioning to the side walls 170, which provides a smooth surface and eliminates snagging of the device when disposed in a pocket or bag. For example, the hinge between the cap and mouthpiece ensures the device remains streamlined, with the hinge not protruding outwardly from the outer profile surface of the cap and housing components, but rather sits flush with the profile surface of the device.

Figure 70:
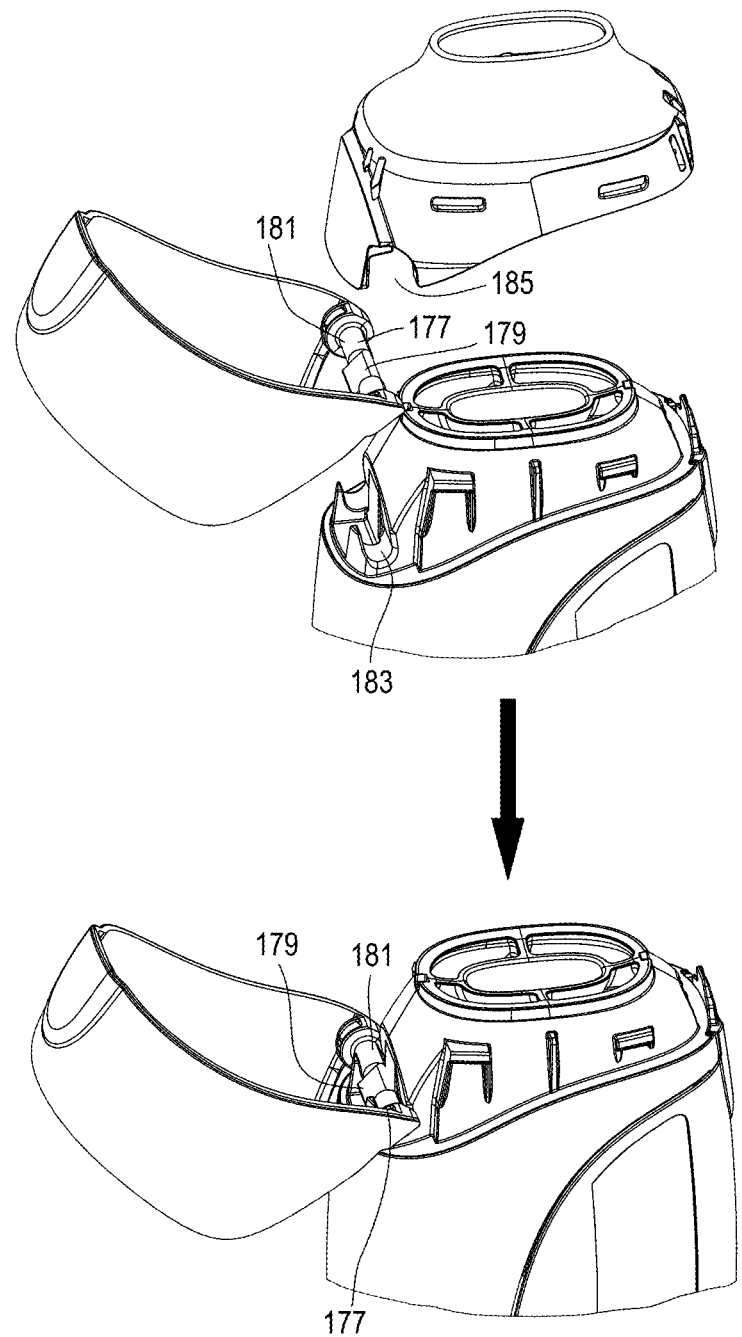
FIG. 70 illustrates an assembly process for one embodiment of a holding chamber.

In one embodiment, shown in FIG. 70, the hinge assembly includes a linear hinge axle 177 extending between opposite sides of the cap side walls 170. The hinge axle 177 has a pair of cylindrical portions 181, and a middle detent portion 179. The detent portion 179 holds the cap in the open position while the device is in use. The detent provides resistance torque throughout the entire rotation of the cap. During assembly, the hinge axle 177 is received in pocket or socket 183 defined by the end portion of the body. The user interface portion has a downwardly facing socket 185 that traps or locks the axle 177 in the socket when the user interface portion is coupled to, e.g., snap fit, the body.

In other embodiments, the cap may be translatably coupled to the user interface portion, for example with a sliding and/or friction fit connection, or may be completely decoupled from the user interface portion, or secured thereto with a tether. A bottom edge of the cap is shaped to mate with the shoulder formed on the user interface portion.

The side wall opposite the hinge has a downwardly opening lip 180, defining a recess thereunder. The tab 130 on the second housing component is captured by the lip 180 and is disposed in the recess when the cap is in a closed position and the first and second housing components are in a closed configuration as shown in FIG. 1, thereby ensuring that the chamber, or first and second housing components, cannot inadvertently open, for example if dropped. The side wall and a portion of the spine wall are configured with a raised profile 182, with an elliptical or obround shape, which provides visual indicia for a user to engage and pivot the cap. The portion of the spine wall may have a slight depression 184, which may receive a user's finger or thumb when lifting the cap.

One side of the cap has a pair of resilient tabs 186 that releasably engage a post 188 having a curved profile on the user interface that defines a portion of the grill defining the exhalation port, with the tabs and post defining a latch. The tabs 186, or fingers, or latch, hold the cap so that it cannot be opened without a user applying a force to the cap lip 180, which biases the tabs around the curved profile until they are disengaged from the post 188. A torsion spring 190 may be disposed around the pivot pin defining the hinge, with the spring engaged between the user interface and the cap to bias the cap away from the user interface and maintain the cap in the open position.

Exemplary materials of the various components are listed in Table 1. Alternatively, the cap may be made of Acetal Celcon M90. The backpiece membrane may be made of Elastosil LR3071/40 (40 durometer) and the substrate may be made of Sabic Valox 420.

Asthmatics commonly experience exacerbated symptoms at night, having difficulty waking up in a darkened room and locating their medication. There is also potential difficulty finding an MDI or holding chamber inside a bag if the area is not well lit. By making the device (e.g., one or more components thereof) glow in the dark, users can quickly locate and administer their medication without needing to turn on a light or fumble in the dark. A glow in the dark capability may be included in the body and/or cap, making them easily visible in dark spaces. By making the device visible in darkness, by including some form of glow in the dark, users will be able to quickly locate their medication in the event they are awoken with an exacerbation. This will minimize stress for the user, as they do not need to expend time and energy fumbling for the device or a light. This has the additional bonus of reducing the disruption to the user's sleep cycle, potentially improving their nights rest. Mixing a glow in the dark additive into the part material for one or more parts may be suitable. This will cause the entirety of any part with the additive included to glow in the dark. In an alternative embodiment, printing on the outside of the device in one or more places may be provided using a glow in the dark ink to produce some light in dark spaces.

TABLE 1

Materials

| Part | Material | Grade | Durometer |
|---|---|---|---|
| Cap | ABS Antistatic | ABS881ASD6T15893 | |
| User Interface | ABS Antistatic | ABS881ASD6T15893 | |
| Body | ABS Antistatic | ABS881ASD6T15893 | |
| Pin | Acetal | Celcon M90 | |
| Valve | Silicone | Momentive LIM6045 | Shore A 45 |
| Backpiece membrane | Silicone | Elastosil LR 3071 | Shore A 30-70 |
| Backpiece Carrier Substrate | PPE + HIPS | Noryl HN731A | |

Assembly

Figure 17:
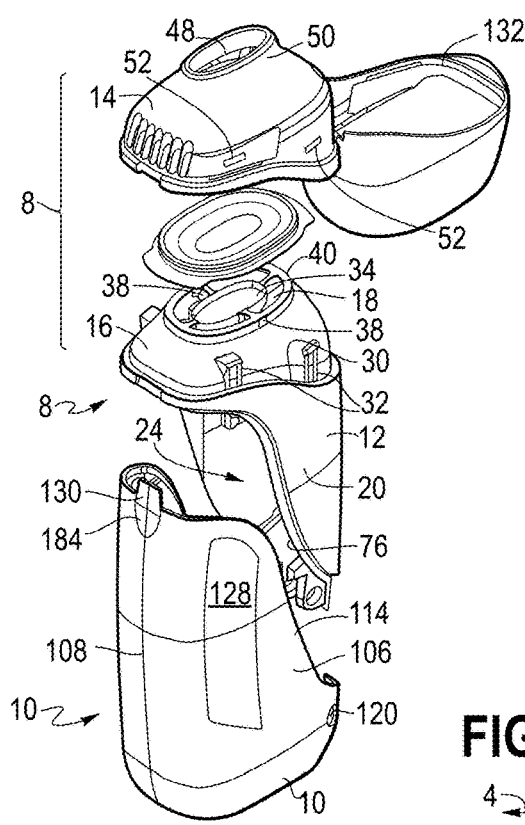
FIG. 17 is a first exploded perspective view of the valved holding chamber.
Figure 18:
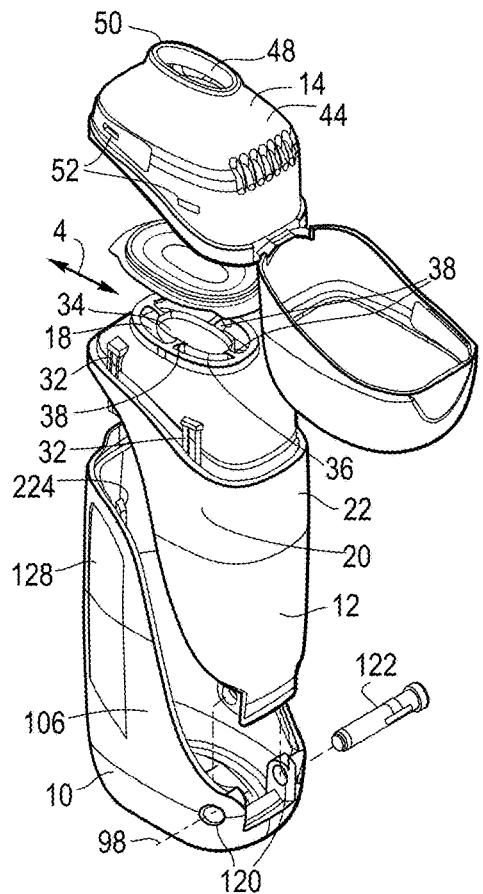
FIG. 18 is a second exploded perspective view of the valved holding chamber.
Figure 19:
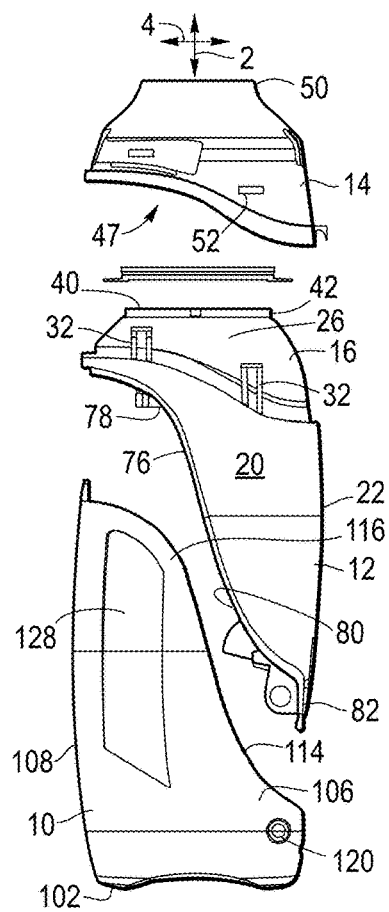
FIG. 19 is an exploded side view of the valved holding chamber.

Referring to FIGS. 17-19, the first and second housing components 8, 10 are pivotally connected with the hinge pin 122 inserted through the hinge components. The first and second housing components are pivotable relative to each other about the pivot axis 98 between a closed configuration, where the edges 76, 112 are abutted and the first and second housing components define an enclosed interior space 24, 110, 118, and an open configuration wherein the first and second housing components are define an access opening 192 communicating with the interior space 118. The latch, or detent, secures the first and second housing components together in the closed configuration.

The backpiece 138 is connected to the second housing component 10 with a snap fit, with the flexible membrane 144 closing the inlet openings 165, 104. The inhalation valve 62 is disposed on the end wall 16 of the first housing component, with the sealing ledge 40 engaging the base portion 72. The user interface 14 is then fitted over the end wall, with the inhalation valve 62, and base portion 72 in particular, being clamped between the user interface and the end wall, with the user interface engaged by the tabs 32 on the end wall.

The cap 132 is coupled to the user interface 14 with at least one hinge pin 178, whether separate or integrally formed, engaging the hinge component 176 on the cap. The cap may be moved from a closed position, wherein the lip 180 of the cap engages the tab 130 of the second housing component and maintains the first and second housing components in a closed configuration, to an open position, wherein the cap, and the lip 180 in particular, is disengaged from the second housing component, or edge thereof, such that the first and second housing components may be pivoted to the open configuration by releasing the latch or detent between the first and second housing components, with the spring 190 biasing the cap to the open position.

In this way, a first latch is moveable between a latched configuration wherein the first latch secures the first and second housing components in the closed configuration and an unlatched configuration wherein the first and second housing components are moveable to the open configuration, and a second latch is moveable between a latched configuration wherein the second latch secures the cap to one of the first and second housing components in the closed position and an unlatched configuration wherein the cap is moveable to the open position. The first latch is moveable from the latched configuration to the unlatched configuration only when the second latch is in the unlatched configuration. As such, the device is provided with a redundant, double-latch system that ensures that the device will not open inadvertently, while also being intuitive to use, meaning that opening the cap, which exposes the mouthpiece, also disengages the second latch such that that the first latch may also be disengaged so that the holding chamber may be opened and the medicament delivery device (e.g., pressurized metered dose inhaler) may be removed.

Referring to FIGS. 3, 16, 47, and 48, the pressurized metered dose inhaler (MDI) 200 includes a canister 202 having a stem 204 and an actuator boot 206. The boot has a chimney 208 defining a cavity 218, a well 216 disposed in the bottom of the cavity and a mouthpiece 210 extending transversely from the chimney. The canister is disposed in the chimney, with the stem received in the well. A top end 212 of the canister may be pushed relative to a bottom of the actuator boot 206, such that that the stem moves relative to the canister and thereby opens a valve to discharge a medicament stored in the container through an outlet formed in the well. The outlet is directed downstream toward the outlet opening 214 of the mouthpiece. The MDI is disposed through the access opening 192 into the interior space 118, with a bottom of the mouthpiece bearing against the inner surface of the backpiece and the engagement ribs 86, 88 engaging a top of the mouthpiece 210. A front 220 of the mouthpiece is engaged by a bearing or engagement surface 92 of the engagement member. A rear surface 222 of the chimney is engaged by a rib 224 formed along an interior of the first housing component.

In this way, the MDI is firmly held in the interior space, and is not permitted to move around. By holding the MDI 200 in a fixed position, it is protected from accidental actuations, any physical damage, and rattling inside the case. The latter is an important factor as this is a portable device, and any tactile or auditory feedback with any movement, such as taking a step with the device inside a pants pocket, could be viewed as an annoyance by the end user. The exact geometries of the various ribs 86, 88, 224 are dependent on the shape and size of the MDI, with the ribs capable of being modified to ensure a snug fit for any manufacturer's design. For example, in one embodiment, a rib 224 in the middle of the inner wall of the second housing component controls the angle the MDI sits at by contacting the rear of the chimney. One or more ribs 86, 88 on the first housing component rotate into position when the body is closed, contacting the top of the MDI mouthpiece 210 and holding it down. The engagement member 84 may be made as a separate part, such that differently shaped engagement members designed to engage different MDI devices may be coupled to the modular holding chamber, for example with a snap fit.

Operation

Referring to FIG. 1, the holding chamber 6 is in a closed configuration, with the cap 132 engaged with the second housing component 10 (body 12 or user interface 14), which is engaged with the first housing component 8. When the device is closed, the cap 132 is latched and will capture at least one of the other of the holding chamber components, such that the housing components 8, 10 cannot rotate open to allow access to the medication (e.g., MDI 200) until the cap 132 has been opened and unlatched. In this way, the cap 132 provides an additional level of security to the MDI in the event of a drop or other impact.

The flexible membrane 144 is in a closed configuration, such that the overall interior space of the chamber 118 is sealed from the ambient environment. A user can look through the first housing component 18 and confirm that an MDI 200 is stored in the holding chamber.

To use the device, the user first opens the cap 132 by gripping the lip 180 of the cap overlying the depression and pivoting the cap to an open position, with the resilient tabs/fingers 186 (i.e., latch) of the cap releasing from the post 188 and the spring 190 biasing/maintaining the cap in the open position. The cap may be opened to an angle of 145 degrees for example, with provides room for the user to access the mouthpiece.

The user may then grasp the side walls 20, 106 of the first and second housing components and pivot the housing components from the closed configuration to the open configuration by disengaging the second latch, such that an access opening 192 is defined and communicates with the interior space 118. The first and second housing component rotate open, up to a 45-degree angle, such that the MDI can be inserted or retrieved comfortably through the access opening 118. The operation of the device is ambidextrous. It should be understood that the term "interior space" refers to the space defined by each of the first and second housing component chamber walls, individually when in an open configuration, and collectively when in a closed configuration. The user may then remove the MDI 200 through the access opening 192, with the MDI being rotated away from engagement from the engagement member 84.

The device must continue to function as a case for the MDI in the event it is dropped or otherwise subjected to a sudden force. If the case were to open during such an event, due to failure of the latching mechanism(s) or any other part of the device, the users medication could fall out and be lost, damaged or otherwise rendered unusable. The two-step opening process, with two separate latching mechanisms, helps ensure the integrity of the system.

While acting as a case for the MDI, the user should be able to quickly and easily retrieve their medication from the device. The opening mechanism has been designed to emphasize ease of access. This is accomplished by splitting the body into two sections along the length of the device, which can hinge about the pivot axis 98 near the backpiece and inlet opening 104. This creates the relatively large access opening 192 and allows the MDI to be retrieved or stored with ease and comfort. The shape of the split is sculpted such that the body is shaped to cradle the MDI while allowing a user access with comfort and ease. In other words, the cavity of the second housing component increases in depth to accommodate and cradle the MDI, and the mouthpiece thereof. As such, a wide opening case provides comfortable storage and retrieval of the MDI inside the VHC. The curve along which the body splits is designed to maximize this ease of use.

After the MDI 200 is removed, the first and second housing components 8, 10 may then be pivoted/rotated back to a closed configuration as shown in FIG. 2 and relatched. The mouthpiece 210 is then inserted through the membrane 144, with the flexible sections 154, 160 moving relative to each other such that the mouthpiece outlet 214 is disposed in the interior space 118. In order to protect the MDI and ensure the inside of the device stays clean, the inlet should be sealed off when not in use. This is accomplished by using a soft material such as silicone to create the resilient flaps or flexible sections, such that when an MDI mouthpiece is inserted, the flaps or flexible sections open inward. When the MDI is removed, the flexible sections return to a neutral, closed off position to protect the interior space inside the body.

The user may insert the mouthpiece 50 into their mouth, with the MDI 200 then being actuated by pressing on the top end 212 of the container and the actuator boot 206 so as to dispense a dose of medicament into the chamber 118. During inhalation by the user, the medicament flows through the outlet opening as the inhalation valve 64 and through the mouthpiece 50 and into the airways of the user. During exhalation, the inhalation valve closes and the exhalation valve 66 opens, allowing air flow through the user interface and out the exhalation port to the ambient environment. After a prescribed treatment, the mouthpiece may be removed from the backpiece, with the user pivoting the first and second housing components 8, 10 to an open configuration. The mouthpiece 210 may then be nested in the second housing component, resting against the rib 224, with the first and second housing components thereafter pivoted to the closed configuration such that the ribs 86, 88 engage the mouthpiece 210 and the detents (i.e., first latch) is engaged. The cap 132 may then be rotated to the closed configuration, with the resilient tabs/fingers 186 (i.e., first latch) engaging the post 188 on the user interface.

The portable holding chamber functions as a storage case for the MDI. While encouraging users to store their MDI inside the chamber, the overall design minimizes the concern of outside contaminants entering the chamber and being inhaled.

In other embodiments, when the MDI is stored inside the device, it may be sterilized to ensure it is clean before each use. This may be accomplished by including an ozone generator 226 inside the device. An interlock will be required as a safety feature to automatically shut off the ozone generator if the chamber is opened. Various levels of user control are possible, from a fully automated cleaning cycle to manual user control at each step. An ozone generator is disposed inside the chamber, and produces ozone when the MDI is stored inside the chamber and neutralize any contaminants. This component will be connected to a safety shutoff, such that if the chamber is opened all ozone generation will stop instantly. Offering the ability to disinfect the MDI while it is stored inside the case ensures the MDI is free of contamination at any time. This may provide the user with peace of mind and encourage using the device as a storage case. The system may have an internal timer, and will generate ozone on a preset schedule, for example once daily at I.OAM for seven minutes (soclean2 default settings). This will simplify the device for the user. Alternatively, the system has an input device, for example a touch screen 228, and an output device, in this example the same touch screen. The user will manually set the length of ozone generation and the start time. The device would allow programming of daily or weekly schedules. The output device would show information such as when the next treatment will begin, if a treatment is active, and the length of time since the most recent treatment. This will give users more control of their device.

As an alternative to ozone treatment, the device may include one or more UV emitters 230, positioned such that the UV light is projected onto both external and internal surfaces of the MDI. The portable VHC is intended to function as a storage case for the MDI. In order to reduce the overall size, the MDI mouthpiece cap is discarded. The VHC should provide at least the same level of protection to the MDI as the mouthpiece cap.

Other Alternative Embodiments:

There is a need for an MDI interface that accepts the mouthpiece of an MDI and couples the MDI to the VHC, and, closes or seals off the opening while the MDI is stored inside the VHC.

Referring to FIG. 49, the MDI inlet 304 may be made of a flexible material, which will have a cork feature or plug 300 on the end of a short tether 302 to be pressed into the inlet when the VHC is not in use. This configuration creates a seal and prevent debris from entering the inlet opening. A single, unitary component includes the MDI inlet 304 and plug 300 with matching geometry, which can be inserted or removed by the user. The plug may be connected to the MDI inlet with the tether 302 of the same material and homogenous, unitary construction. Using a single, unitary piece creates an MDI interface that accepts the mouthpiece of an MDI and couples the MDI to the VHC, and, closes or seals off the opening while the MDI is stored inside the VHC.

Referring to FIG. 50, the MDI inlet 308 may be made of flexible material, which will be fixed to a plug 310, made of a rigid material and fixed, for example, with an adhesive, mechanical, or chemical bond. The point of connection is hinged to allow the plug 310 to rotate away inside the chamber from the aerosol pathway when an MDI is inserted. The inlet 308 and hinge 312 may be integrally formed and unitary, with the hinge 312 having an undercut allowing it to pivot relative to the inlet. The plug is connected for example with a snap-fit insert member 314 having a catch inserted through an opening 316 in a flange 318. The plug 310 blocks the opening in the MDI interface when an MDI is not inserted. By molding the hinge flange 318 at an angle relative to a plane defined across the opening for the MDI, the flange 318, or hinge 312 has a preload, allowing it to function as a spring and force the plug closed over the inlet opening. When an MDI is inserted, the configuration of the plug is such that it will rotate clear of the MDI mouthpiece inside the holding chamber. The plug may be formed with a tapered surface 320, which functions like a cam and follower mechanism, such that the plug will move or rotate, and be biased by the MDI, parallel to the chamber and flow path and rest against the interior side wall of the holding chamber, but outside the aerosol plume. Using a system of a flexible interface and hinge together with a more rigid plug creates an MDI interface that accepts the mouthpiece of an MDI and couples the MDI to the holding chamber, and, closes or seals off the opening while the MDI is stored inside the holding chamber. In this way, the system is configured with a self-closing system, with the hinge acting as a closing device, or biasing member. Other springs may be provided to further bias the plug to a closed position.

Figure 51:
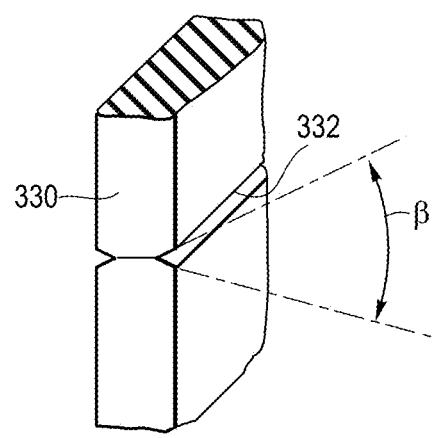
FIG. 51 is a cross-sectional view of a portion of a valved holding chamber with an alternative backpiece.

Referring to FIG. 51, the MDI inlet 330 will be made of a flexible material, which will contain several flaps that form a flat surface across the MDI inlet. The flaps will return to the closed position when the MDI is stored inside the chamber, and will open inward when the MDI is inserted. The backside of the flaps defining the slit each have an angled chamfer 332, defining an angle β, at the corner thereof, which allows the flaps to align when closing.

Figure 52:
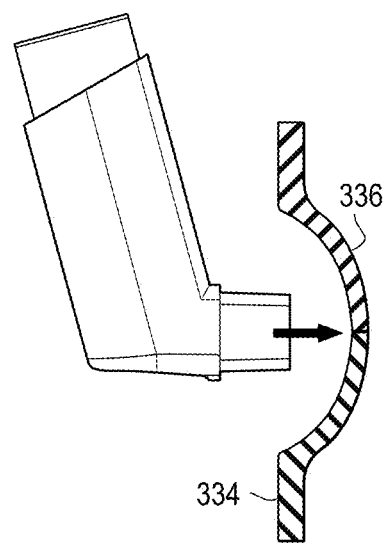
FIG. 52 is a cross-sectional view of a portion of a valved holding chamber with an alternative backpiece.

Referring to FIG. 52, the flaps 334, in a closed position, form a slight dome 336, with a concave surface facing the MDI. By forming the flaps into a concave dome in the closed position, the flaps will close correctly and uniformly and more reliably than if the closed surface was flat.

Figure 53:
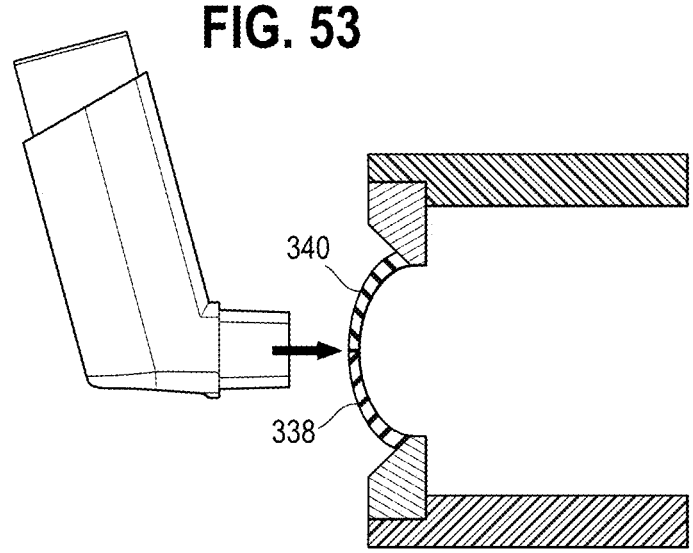
FIG. 53 is a cross-sectional view of a portion of a valved holding chamber with an alternative backpiece.

Alternatively, and referring to FIG. 53, the flaps 338 return to a position to form a slight dome 340 that is convex with respect to the MDI. By forming the flaps into a convex dome in the closed position, the inlet will be stable in the closed position and resist entry from foreign bodies such as dust and lint.

Figure 54:
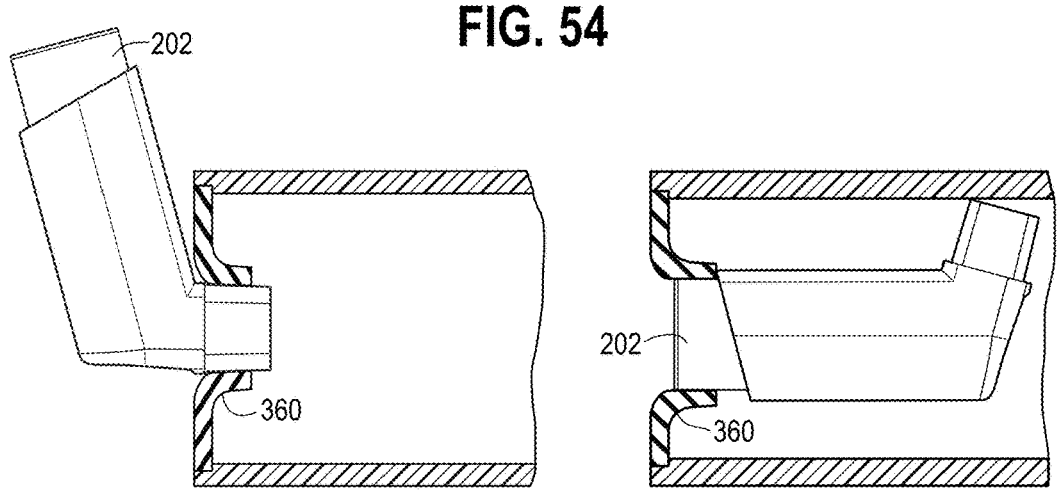
FIG. 54 is a cross-sectional view of a portion of a valved holding chamber with an alternative backpiece.

Referring to FIG. 54, the holding chamber acts as a storage case for the MDI when not in use. By inserting the MDI canister 202 into the interface from inside the holding chamber, the standard diameter of canisters, e.g., asthma rescue medication canisters, may be leveraged by designing the MDI interface such that the canister can be inserted to create a seal. This removes the need for addition parts or material to close off the MDI interface when the canister is in a stored position. Specifically, the MDI canister 202 is inserted into the MDI interface 360 to seal the opening when the MDI is being stored inside the holding chamber. Using the MDI canister to seal the MDI interface of the holding chamber when in the storage configuration. Eliminating the need for a separate feature to seal the interface simplifies the design and reduces costs. The flaps are sufficiently flexible that they may be further flexed to accommodate the mouthpiece of the MDI when the MDI is removed from the holding chamber and inserted into the interface.

Figure 55:
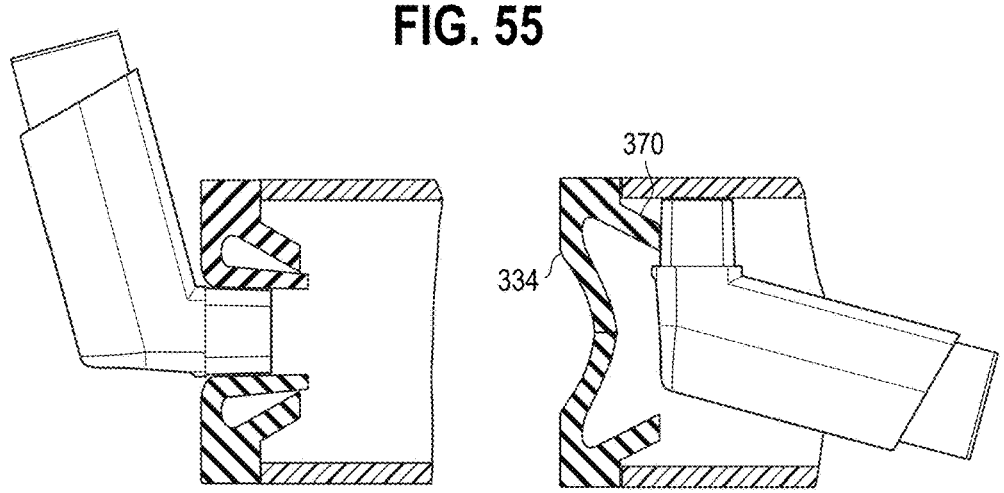
FIG. 55 is a cross-sectional view of a portion of a valved holding chamber with an alternative backpiece.

Referring to FIG. 55, a flexible element 370 extends into the interior of the holding chamber and contacts the MDI before it can compress against the MDI interface. The flexible element 370 may be integrally formed with the MDI interface 334, which will compress when the MDI is stored inside the holding chamber without allowing the flaps to open. The flexible elements 370 will open along with the flaps in the interface when the MDI is inserted for use. The flexible element will work to capture the MDI and prevent rattling, while protecting the flaps on the MDI inlet from being forced open by the MDI. This will provide better protection of the device from physical damage and contamination from outside the storage case.

Figure 56:
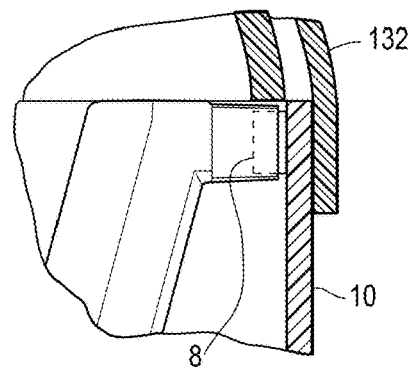
FIG. 56 illustrates the opening sequence of the valved holding chamber.

The device must continue to function as a case for the MDI in the event it is dropped or otherwise subjected to a sudden force. If the case were to open during such an event, due to failure of the latching mechanism(s) or any other part of the device, the user's medication may fall out and be lost, damaged or otherwise rendered unusable. As disclosed above, and shown in FIG. 56, the VHC body will be made of two halves 8, 10 joined with a hinge such that the body can open to enable access to the MDI inside. These two halves will latch together with a detent, which is susceptible to failing in the event of a drop or impact. The mouthpiece cap 132 fits over top of an extension of the lower body half in such a way that the body will not be able to open until the cap has been lifted. The cap is held in place by a snap fit interface with the mouthpiece of the VHC. The lower body half 10 has an extended tab that overlaps with the upper body half 8 when they are latched shut by a detent feature. The mouthpiece cap 132 captures the tab in the closed position and lock the body halves together until the cap is opened. The cap will have a snap fit or other latching mechanism to hold it in the closed position. These two latching mechanisms ensure retrieving the MDI will require two distinct actions. A unique solution utilizing existing parts of the device to create a two-step opening process with two separate latching mechanisms to be overcome. By using existing parts and steps which must be carried out to use the VHC to deliver medication, extra protection does not complicate the usage of the device. This will ensure a single impact or drop cannot cause the MDI contained inside the VHC to be released from the carrying case.

Figure 57A:
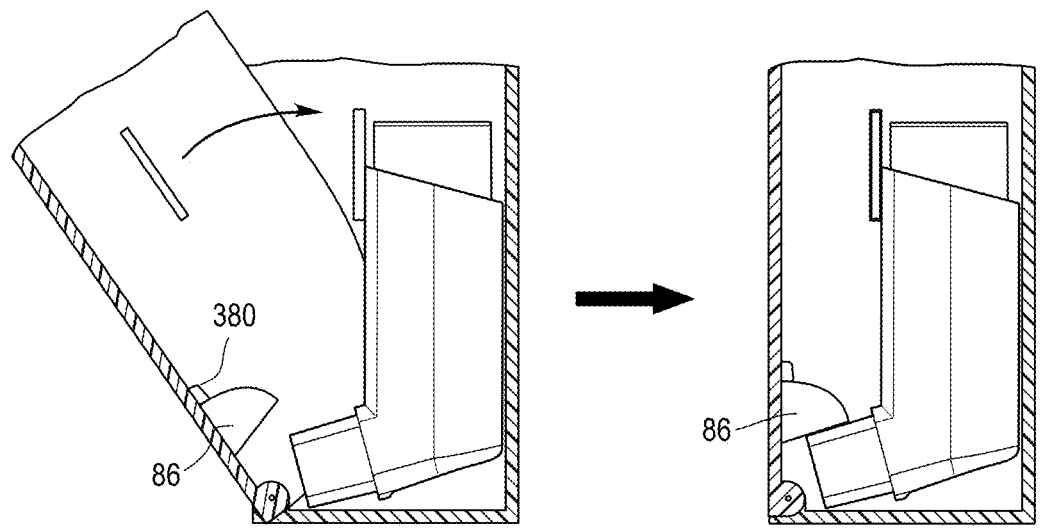
FIGS. 57A and B shows an alternative embodiment of an anti-rattle feature.
Figure 57B:
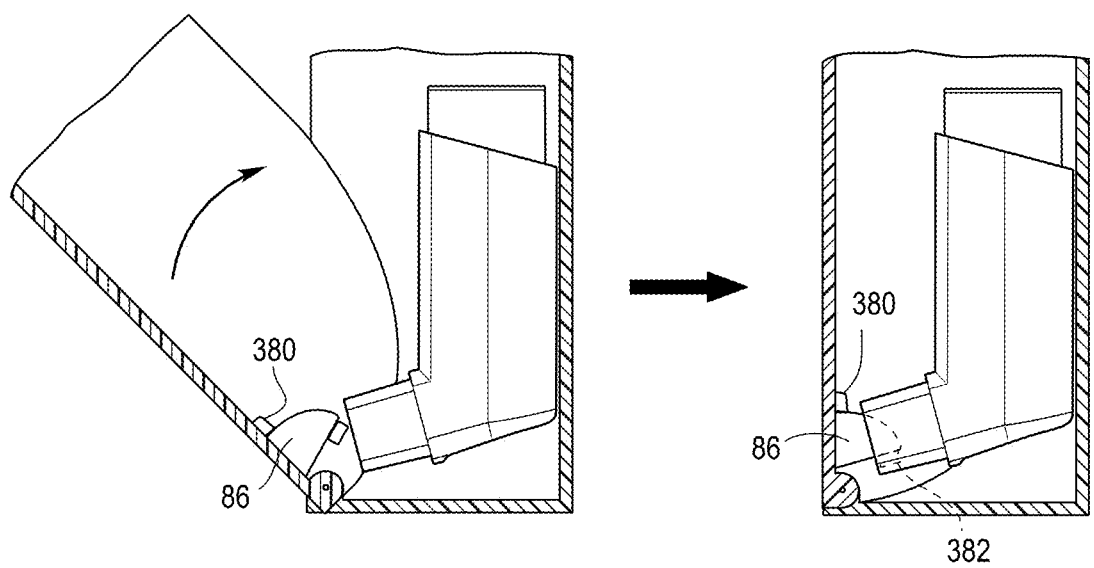

Referring to FIGS. 57A and B and 74A and B, the MDI must be sufficiently constrained inside the device, when acting as a storage case, to not rattle during normal movement. This will protect the MDI from any damage inside the case, and remove the possibility of an accidental actuation of the canister. The device is intended to be carried in a pocket, and the tactile and auditory feedback of the MDI knocking against the inner walls of the VHC could be perceived by users as an annoyance, influencing their willingness to carry the device. A set of ribs 86, 88 on the internal surface of the holding chamber, with geometries designed to capture the mouthpiece design of each, differently shaped MDI. The ribs will be on one half of the body, such that when the device is opened they rotate to allow space for the MDI to sit in the VHC, and when the body is closed the ribs come into contact with the MDI to fix it against the VHC and prevent movement. The first shape of MDI to be accommodated, shown in FIG. 57A, will be captured by a system of two ribs 88, consisting of a rib with a flat bottom which will capture the mouthpiece of the MDI between the rib and bottom of the VHC to hold it down, alongside a vertical rib which will capture the sides of the VHC and prevent rotation. The second shape, whosn in FIG. 57B, will use the rest of the geometry, or shoulder 380, on the first rib 86 to hold the MDI up, while another rib, or end portion 382 thereof, will hold the MDI down. The top of the first rib has a flat face to prevent the MDI from rotating. Both ribs in this case are disposed inside the mouthpiece, and contact the internal faces of the MDI mouthpiece. In this way, the same ribs may engage different MDI configurations to capture and hold the MDI and prevent rattling inside the case. Preventing the MDI from rattling inside the VHC will serve to give users an impression of quality and thoughtfulness in the design of the VHC. The geometries of the anti-rattle ribs may be modified to accommodate alternative styles of MDI design, using the same concept to capture alternative shapes and sizes in the same manner.

Figure 58:
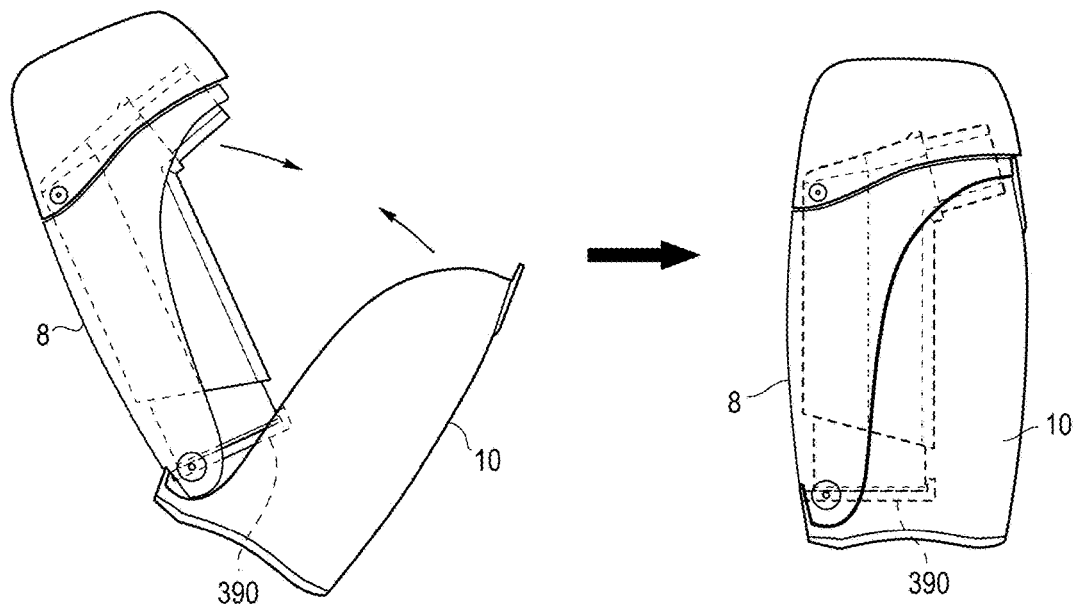
FIG. 58 shows an alternative embodiment of an anti-rattle feature.

Referring to FIG. 58, ribs 390 or grips made of a flexible material inside the holding chamber, which can conform to the shape of multiple MDIs, each with unique geometries. These flexible elements could exist in various sizes, shapes, and locations. Flexible elements inside the holding chamber capture an MDI and prevent movement or rattling inside the chamber. Using one feature to capture multiple styles of MDI by making the ribs flexible, avoiding reliance on very specific geometry. Preventing the MDI from rattling inside the VHC will serve to give users an impression of quality in the design.

Figure 59:
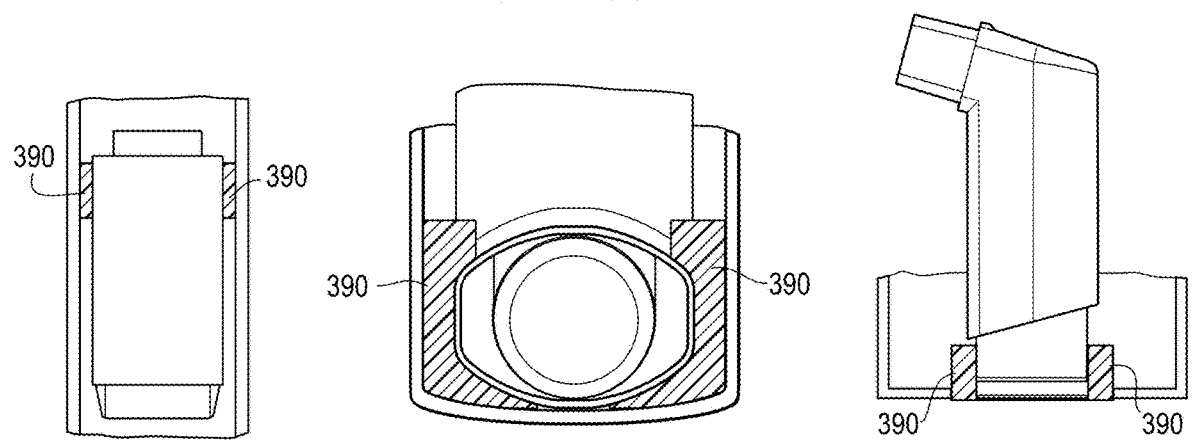
FIG. 59 shows an alternative embodiment of an anti-rattle feature.

Flexible ribs may be disposed on opposing inner faces of the chamber, such that the MDI will be gripped between them. Flexible elements may be disposed on the bottom or sides of of the holding chamber such that the mouthpiece of the MDI will be unable to move once inserted. The ribs will capture the mouthpiece and apply pressure on the sides and top of the part to hold it in place. As shown in FIG. 59, flexible element 390 may be disposed on the sides or the bottom of the holding chamber, such that the canister of an MDI will be captured along its circumference when the MDI is inserted canister first into the case. This is a similar design to the inlet seal using MDI canister.

Referring to FIG. 60, an elastic band 400 runs along each side of the inside of the holding chamber, and may include a single band looped around the inside of the chamber. The elastic bands 400 are integrated into the opening and closing of the holding chamber body such that when an MDI is inside the holding chamber as it closes, the elastic bands, which extend between the housing components 8, 10, will capture or squeeze the MDI and prevent movement inside the chamber. Incorporating an elastic into the opening of the VHC to grip the sides of any MDI inside the case. Using an elastic to capture multiple styles of MDI, avoids reliance on different specific geometries associated with different MDI's. Preventing the MDI from rattling inside the VHC will serve to give users an impression of quality and thoughtfulness in the design of the VHC.

Referring to FIG. 61, one or more plastic ribs 420 on the inner walls of the holding chamber may capture the MDI when inserted straight in from the bottom. The bottom will act as a lid and capture the MDI against the ribs. The ribs 420 may be rigid, or hard, and disposed on either side of the holding chamber, which will fix the MDI in place when the cap 132 is closed over top of the MDI. Using a single rib may capture multiple styles of MDI by using an alternative opening style, avoiding reliance on very specific geometry.

Referring to FIG. 62, a rib 420 on the inner walls of the holding chamber may capture the MDI when inserted straight in from the bottom. The rib 420 will fit in the space between the MDI canister and the plastic MDI boot, with the bottom acting as a lid to hold the MDI down against the rib. A rib 420 on the inner wall of the VHC is positioned such that when an MDI is inserted, the rib will slot, or be inserted into the MDI between the boot and canister, which will fix the MDI in place when the cap 132 is closed over top of the MDI. Using one rib design to capture multiple styles of MDI by using an alternative opening style, avoiding reliance on very specific geometry.

Volume and length have a direct correlation to the aerosol output of a VHC, so while it is desirable to reduce the size of the holding chamber, performance must be maintained. The size of the device, as well as the specifics of the shape and overall dimensions and feel of the device, will impact how portable it is.

Figure 63:
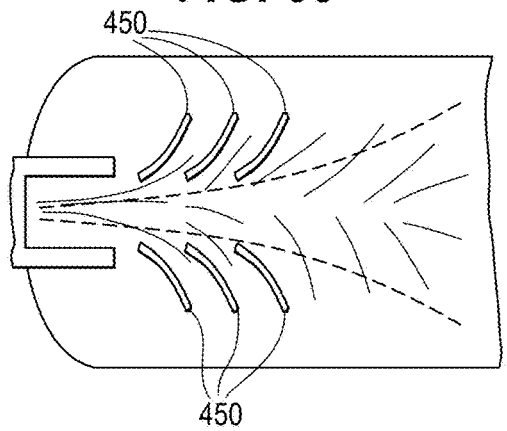
FIG. 63 is a partial cross-sectional view of one embodiment of a valved holding chamber with a suppressor feature.

Referring to FIG. 63, by designing the holding chamber to slow down aerosol as it enters the chamber, better aerosol delivery may be accomplished in a smaller chamber. A series of baffles or deflectors 450 inside the chamber will cause entrained air to be redirected laterally to slow the central aerosol plume. Baffles 450 are included inside the main body of the holding chamber, positioned such that the baffles are outside of the central aerosol plume. The baffles extend radially outwardly and in a downstream direction from a central location. The baffles 450 deflect entrained air laterally, slowing the aerosol plume, reducing impaction inside the holding chamber and reducing the amount of drug exiting the mouthpiece when the MDI is fired. Using baffles inside the holding chamber to slow the aerosol plume and improve drug output of the holding chamber. This will allow the size of the holding chamber to be reduced without detrimental effects on drug delivery.

Figure 64:
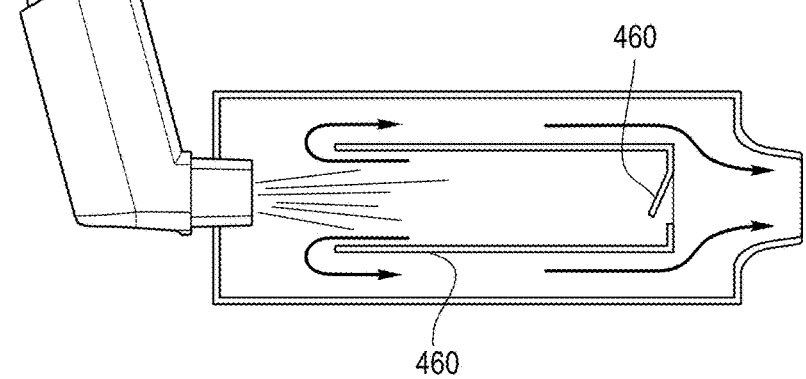
FIG. 64 is a partial cross-sectional view of one embodiment of a holding chamber with a counter-flow feature.

Alternatively, the VHC may be designed to provide counter flow, as shown in FIG. 64. Many current chambers use a "flow through" aerosol path. Pressure generated by the MDI firing can open the inhalation valve and aerosol may be lost if the chamber is too small. Altering the flow path may prevent these losses. Aerosol will be directed into a closed section 460 of the VHC, which defines a cavity having an open at an upstream end and which is closed at a downstream end, where the air will act as a cushion, slowing the plume. The closed section 460 in the center of the VHC with a one-way valve 462 to allow airflow during inhalation and prevent flow through the central section when the MDI is fired, causing a pressure increase in the chamber. The air cushion created by closing the valve 462 will slow the aerosol plume and prevent drug loss during MDI firing. Altering the flow path of aerosol within the holding chamber with a closed off section in the middle containing an air cushion. This will slow the aerosol plume when an MDI is actuated in the MDI, improving drug delivery for the user.

In another embodiment, the VHC employs active counter flow. There is the possibility of producing a counter flow to slow the aerosol plume, using a fan or similar style of device inside the VHC. This could be linked with actuation detection as to only activate when needed, saving on power consumption. The existing air current or increased pressure in the VHC will serve to slow the aerosol, improving drug delivery and device performance.

Smart Features:

Without a dose counter, it is impossible for users to know exactly how much medication is left inside their MDI canister. In markets without dose counters built into the MDI, patients have difficulty knowing when they need to refill their prescription. This issue is made worse as the MDI will continue to fire an aerosol plume of pure propellant once the medication has been depleted. This could lead to untreated exacerbations in an emergency.

Figure 31:
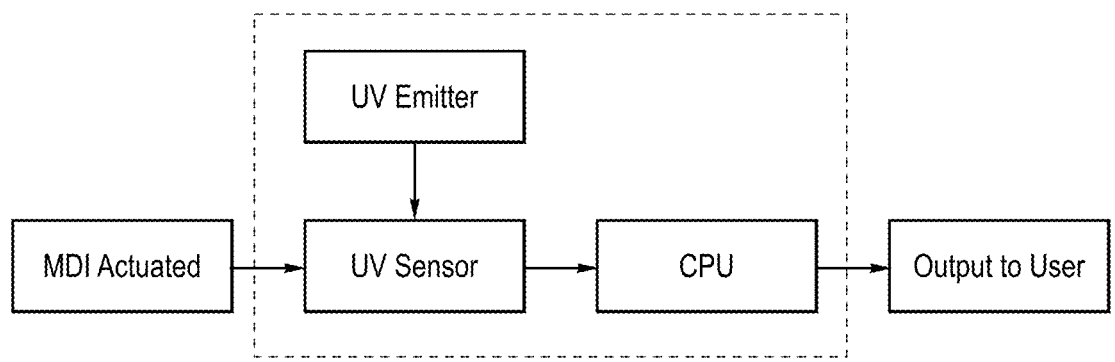
FIGS. 31-39 show alternative flow diagrams for various embodiments of a valved holding chamber.

A drug detection system which functions by taking advantage of Albuterol's absorption of light in the ultraviolet spectrum, specifically, in this case, at a wavelength of 275 nm. Referring to FIG. 31, using an ultraviolet light emitter and corresponding sensor to measure the intensity of ultraviolet light inside the holding chamber, the system can measure how much medication is inside the chamber. A system includes an ultraviolet light emitter of the appropriate wavelength to be absorbed by Albuterol and a corresponding analog ultraviolet light sensor, to measure the amount of medication being delivered by the MDI. The sensor and emitter will be mounted such that the MDI plume will come between the emitter and sensor. Including an ultraviolet light emitter and sensor in the body of the VHC. This system will allow users to know when their MDI is running out of medication without an explicit dose counter.

Figure 32:
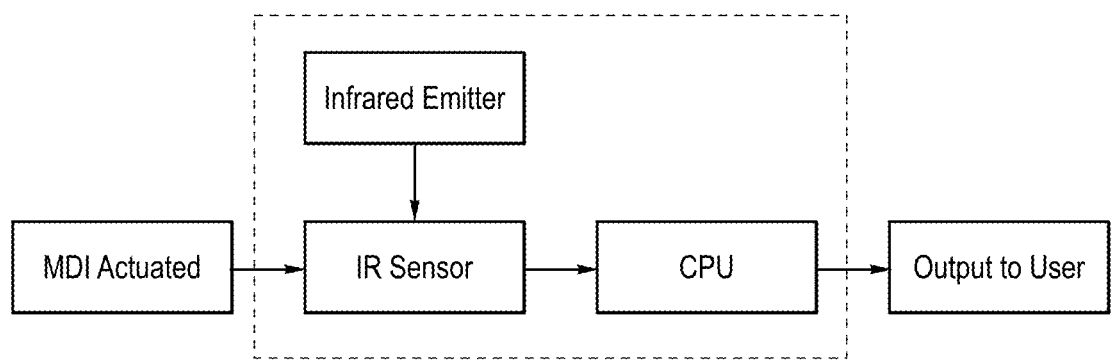

Referring to FIG. 32, a propellant detection system which functions by taking advantage of MDI propellant's absorption of light in the infrared spectrum. Using an infrared light emitter and corresponding sensor to measure the intensity of infrared light inside the holding chamber, the system can measure how much propellant is inside the chamber. As the MDI runs out of medication, a larger fraction of the plume will be made up of propellant. A system includes an infrared light emitter of the appropriate wavelength to be absorbed by propellant and a corresponding analog infrared light sensor, to measure the amount of propellant present in the holding chamber. The sensor and light source will be mounted such that the MDI plume will come between the emitter and sensor. Including an infrared light emitter and sensor in the body of the holding chamber. This system will allow users to know when their MDI is running out of medication without an explicit dose counter.

Figure 33:
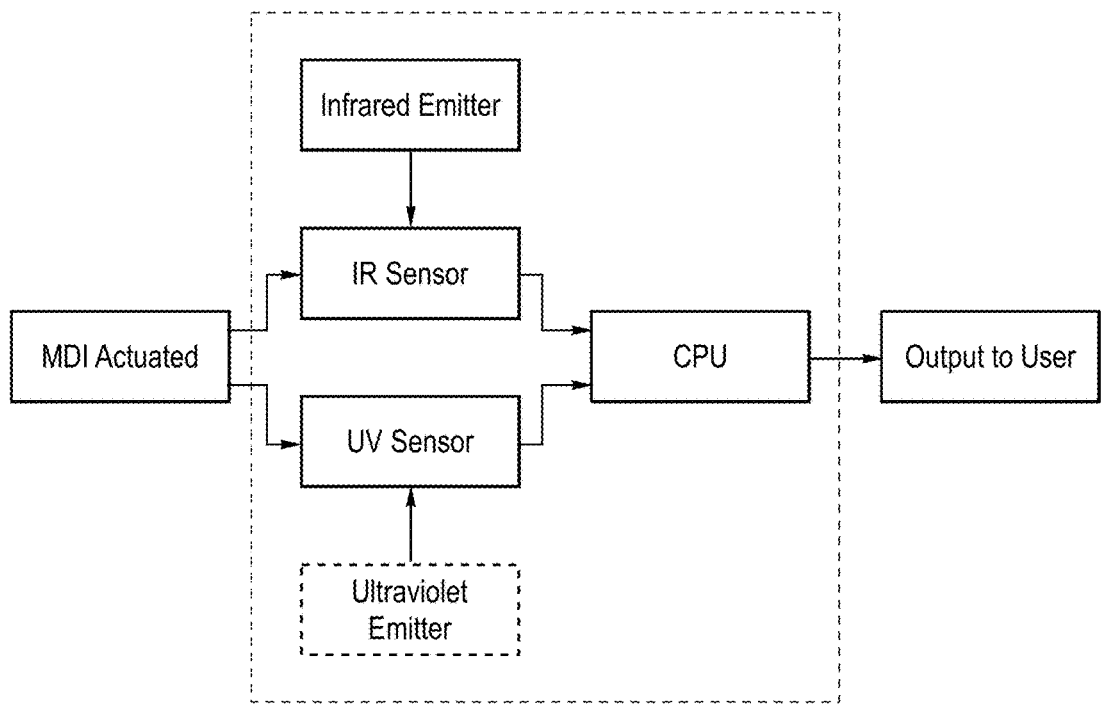

Referring to FIG. 33, an Albuterol and propellant measurement system functions by taking advantage of Albuterol's absorption of ultraviolet light, and propellant's absorption of infrared light. Using an ultraviolet light emitter and corresponding sensor to measure the intensity of ultraviolet light inside the VHC, alongside an infrared light emitter and corresponding sensor to measure the intensity of infrared light inside the holding chamber, the system can measure the amount of propellant and drug in the aerosol plume. This will allow the composition of the aerosol plume to be quantified. A system includes an ultraviolet light emitter of the appropriate wavelength to be absorbed by Albuterol, a corresponding analog ultraviolet light sensor, to measure the amount of medication inside the VHC, an infrared light emitter of the appropriate wavelength to be absorbed by the propellant and a corresponding analog infrared light sensor, to measure the amount of propellant inside the VHC. The sensor and emitter pairs will be mounted such that the MDI plume will come between the emitter and sensor. Including an infrared light emitter and sensor, and an ultraviolet light emitter and sensor in the body of the VHC. This system will allow users to know when their MDI is running out of medication without an explicit dose counter.

Figure 34:
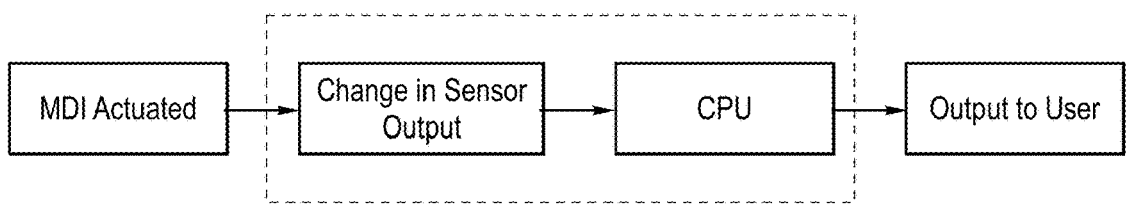

Referring to FIG. 34, a sensor measures the amount of a specific component in the aerosol plume. By mounting the sensor inside the body of the holding chamber, the system can use sensor values to determine how many doses remain inside the MDI. A system includes a sensor mounted inside the holding chamber body to measure the aerosol plume. Including a sensor to take readings of the aerosol plume inside the holding chamber body. This will allow users to know when their MDI is running out of medication without an explicit dose counter.

Figure 35:
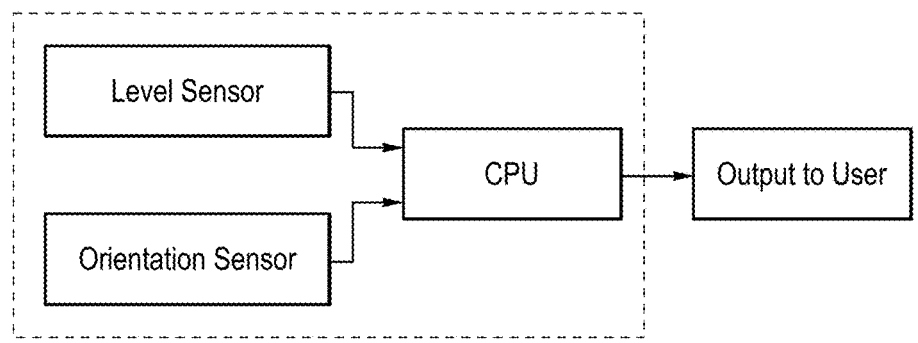

Referring to FIG. 35, the level of liquid inside the MDI canister indicates how much medication remains. This can be accomplished using an ultrasonic level sensor, mounted inside the holding chamber such that the canister sits against the sensor when in storage inside the holding chamber. A sensor to determine orientation such as a gyroscope, accelerometer, or magnetometer, will ensure measurements are taken in a consistent orientation. An ultrasonic sensor secured to the holding chamber on the inner wall opposing the anti-rattle ribs. The sensor will be directly adjacent to the MDI canister when the MDI is stored inside the device. A sensor with output data specifying orientation. The smart system will be able to use the sensor readings to recognize the amount of medication remaining. Using an ultrasonic sensor to check the level of liquid inside the MDI canister, along with an orientation sensor to ensure readings are taken in a consistent and repeatable position. This will allow users to know when their MDI is running out of medication without an explicit dose counter.

For any of the above concepts, the smart holding chamber can use sensor data to determine the cause of an incomplete dose of medication. Output to the user could inform them of the lapse in technique and coach the user on how to obtain a better delivery of medication for the next dose. Users sometimes associate the sensation of taste with a dose of medication and feel they did not get their dose when there is no immediate feedback. The system could also have outputs in the case of a correct dose designed to create a sensation or association for user to replace the taste of aerosol in the mouth one experiences when using the MDI alone.

Asthma attacks can be triggered by environmental influences in a specific locality. By recording the location a chamber has been used, and mapping this data over time, higher risk locations for an exacerbation can be identified, providing asthmatics with a better understanding of their condition. A wireless module capable of connecting to smart device, mounted to the VHC, would allow the location data of the smart device to be recorded when the chamber is in use. After tracking this data over time, the system can detect patterns in the locations where exacerbations are occurring. A module capable of wireless connection with a smart device included in the Smart VHC system, to inform the smart device when an MDI is fired inside the chamber and record the location from the devices GPS or cellular signal. Including the ability to pair the MDI wirelessly with a smart phone such that the two devices can communicate information. Recognizing patterns in the locations of exacerbations and passing this information along to the user can lead to increased awareness and control of their asthma.

Figure 36:
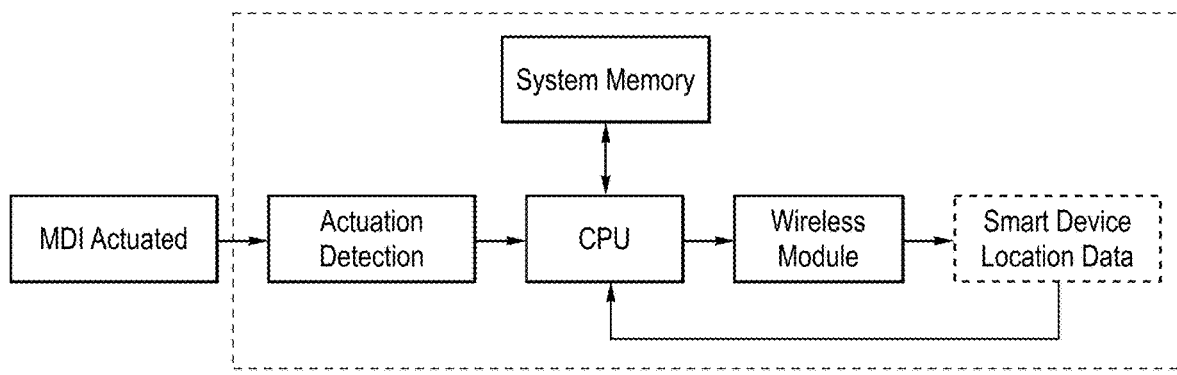

Referring to FIG. 36, a module capable of connecting to a worldwide network (such as cell towers or GPS satellites) mounted to the holding chamber would allow the location data to be recorded when the chamber is in use. After tracking this data over time, the system can detect patterns in the locations where exacerbations are occurring. A module capable of tracking location included in the Smart holding chamber system, to be polled for location data when an MDI is fired inside the chamber. Including a location tracking component in the Smart VHC system. Recognizing patterns in the locations of exacerbations and passing this information along to the user can lead to increased awareness and control of their asthma.

The device will function as a carrying case for the MDI. A patient in a rush could carry the device with them, not realizing their rescue MDI was not contained inside the device. One could also forget the case itself. Including wireless capabilities in the VHC would allow for the device to connect with a user's phone when in range. If the phone is taken out of range of the device, for example a user leaving home without their VHC, the wireless connection will be lost between the VHC and cellular device. At this point the cell phone could produce a notification with the last known location of the device, informing the user they may have forgotten it. A system comprising: a module capable of wireless communications mounted to the VHC, to be paired with a mobile device. When connection is lost the mobile device will display a notification with the last known location of the VHC. Including the ability to pair the VHC wirelessly with a cell phone. Notifying users when they are not within range of their VHC could improve chamber use by encouraging users to carry the VHC with them, and prevent untreated exacerbations if the device is not with them. This will also help users to locate their device if it has been lost or misplaced.

Figure 37:
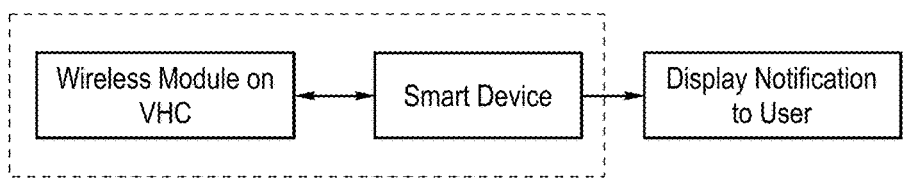

Referring to FIG. 37, including wireless capabilities in an attachment to fit onto the MDI to connect with a mobile device. If the phone is taken out of range of the MDI, the wireless connection will be lost. At this point the cell phone could produce a notification with the last known location of the MDI, informing the user they may have forgotten it. A system includes a module capable of wireless communications included in the MDI to be paired with a mobile device and a form fitting attachment to the MDI containing the wireless modules, such that it does not interfere with use of the MDI or delivery of the medication. When connection is lost the mobile device will display a notification with the last known location of the MDI. Including the ability to pair the MDI wirelessly with a cell phone. Notifying users when they are not within range of their holding chamber could prevent untreated exacerbations. This will also help users to locate their MDI if it has been lost or misplaced.

Figure 38:
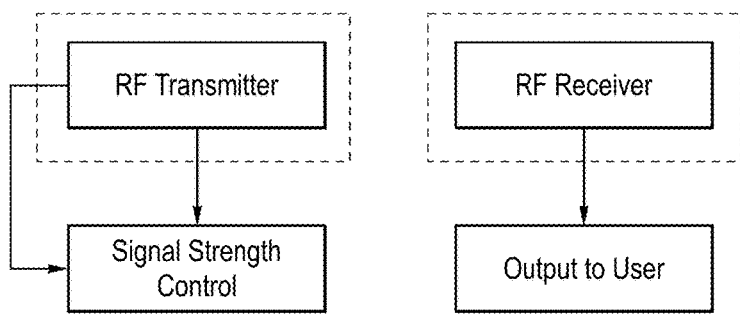

Referring to FIG. 38, including a radio signal transmitter in the VHC would allow it to connect with a receiving device. Should the receiver lose contact with the VHC, it would produce a notification or signal that the connection has been lost. By including a method for the user to control the signal strength, the range at which connection is lost can be adjusted according to preference. A system includes a radio frequency transmitter mounted in the VHC, a potentiometer or other interface to control the signal strength of the transmitter and a receiver which can notify the user should the signal between transmitter and receiver be lost. This would help users to realize if they have forgotten the holding chamber. Including a potentiometer to adjust the transmitted signal would give the user control over the maximum distance before being notified. Including a RF transmitter in the holding chamber, with supporting hardware to allow user control of the range of the signal. The receiving device must be carried by the users, to function properly and inform users when they are not within range of their holding chamber which could prevent untreated exacerbations. To encourage carrying the receiver, it could be built into a medic alert bracelet, adding more value for the user.

Figure 39:
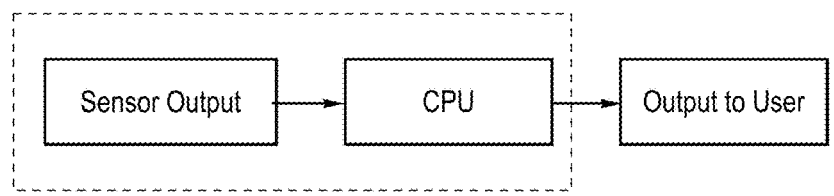

Referring to FIG. 39, using a limit switch or other simple sensor to determine the presence of the MDI inside the chamber. The smart system could use this to determine if there is not an MDI inside the case. A simple senor positioned inside the chamber such that the presence of an MDI inside the case will produce a change in output values. Sensors could include, but are not limited to a limit switch and/or a ultrasonic, optical or pressure sensor. This system would allow the device to inform the user if their puffer is not contained in the VHC. By using a simple sensor, costs could be lower compared to more complex reminder systems.

Without being aware that the MDI has been actuated, data recording/tracking features included in the smart system will not be able to function properly.

By including a sensor or a system of sensors in the VHC, the smart system will recognize when the MDI has been actuated and aerosol is deposited into the chamber. The sensor(s) included in the VHC could be any combination of the following, allowing the smart system to detect when the MDI has been actuated while coupled to the MDI inlet.

Microphone to detect the sound profile of an MDI canister being actuated.
Pressure sensor to detect the internal pressure increase of the chamber.
Sensors for detecting the propellant or another chemical in the aerosol plume (including the IR drug tracking for dose counting purposes)
Force sensor (on top of MDI canister, or elsewhere near the MDI, likely in the MDI adapter)
Airflow sensor (hotwire MEMS)
Optical sensor could detect the plume in the moments before it disperses
IR/UV solutions for drug detection
Gyroscope/Accelerometer to ensure the MDI canister is oriented vertically
A smart system capable of detecting when an MDI is actuated while coupled to the MDI inlet on the VHC. This could provide users with a form of drug detection, technique coaching, or dose counting, improving their asthma and resulting in better clinical outcomes.

A smart system capable of detecting when an MDI is actuated while coupled to the MDI inlet on the VHC. This could provide users with a form of drug detection, technique coaching, or dose counting, improving their asthma and resulting in better clinical outcomes.

Although the present invention has been described with reference to preferred embodiments. Those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. A holding chamber configured to enclose and carry a pressurized metered dose inhaler, the holding chamber comprising:
   a first housing component comprising a user interface comprising an outlet opening;
   a second housing component comprising an inlet opening spaced apart from the outlet opening of the first housing component, wherein the inlet opening comprises a sealable backpiece configured to receive a mouthpiece of the pressurized metered dose inhaler, wherein the first housing component is pivotally connected to the second housing component about a pivot axis, wherein the first and second housing components are pivotable relative to each other about the pivot axis between a closed configuration, wherein the first and second housing components define an enclosed interior space, and an open configuration, wherein the first and second housing components are spaced apart and define an access opening communicating with the interior space; and
   a cap moveably connected to one of the first and second housing components, wherein the cap is moveable between a closed position, wherein the cap engages the other of the first and second housing component and maintains the first and second housing components in the closed configuration, and an open position, wherein the cap is disengaged from the other of the first and second housing component such that the first and second housing components are capable of being pivoted to the open configuration.

2. The holding chamber of claim 1 further comprising a spring biasing the cap to the open position.

3. The holding chamber of claim 1 wherein at least one of the cap and the other of the first and second housing component comprises a latch moveable between a latched configuration, wherein the latch secures the cap to the other of the first and second housing components in the closed position, and an unlatched configuration, wherein the cap is moveable to the open position.

4. The holding chamber of claim 3 wherein the latch comprises a first latch, and further comprising a second latch moveable between a latched configuration, wherein the second latch secures the first and second housing components in the closed configuration, and an unlatched configuration, wherein the first and second housing components are moveable to the open configuration.

5. The holding chamber of claim 4 wherein the second latch is moveable from the latched configuration to the unlatched configuration only when the first latch is in the unlatched configuration.

6. The holding chamber of claim 3 comprising a biasing member maintaining the cap in the open position when the latch is in the unlatched configuration.

7. The holding chamber of claim 1 wherein at least one or both of the first and second housing components comprises an engagement member disposed in the interior space, wherein the engagement member is adapted to engage a medicament delivery device disposed in the interior space, and wherein the interior space is dimensioned to receive the medicament delivery device when the first and second housing components are in the closed configuration.

8. The holding chamber of claim 7 wherein the engagement member comprises a first rib disposed on the first housing component, wherein the first rib is shaped and dimensioned to engage the medicament delivery device.

9. The holding chamber of claim 8 further comprising a second engagement member comprising a second rib disposed on the second housing component, wherein the second rib is shaped and dimensioned to engage the medicament delivery device.

10. A holding chamber configured to enclose and carry a pressurized metered dose inhaler, the holding chamber comprising:
    a first housing component comprising a user interface having an outlet opening; and
    a second housing component having an inlet opening spaced apart from the outlet opening of the first housing component, wherein the inlet opening comprises a sealable backpiece configured to receive a mouthpiece of the pressurized metered dose inhaler, wherein the first housing component is pivotally connected to the second housing component about a pivot axis, wherein the first and second housing components are pivotable relative to each other about the pivot axis between a closed configuration and an open configuration;
    a first latch moveable between a latched configuration wherein the first latch secures the first and second housing components in the closed configuration and an unlatched configuration wherein the first and second housing components are moveable to the open configuration;
    a cap movably connected to one of the first and second housing component, wherein the cap is moveable between a closed position, wherein the cap engages the other of the first and second housing components and maintains the first and second housing components in the closed configuration, and an open position, wherein the first and second housing components are capable of being pivoted to the open configuration; and
    a second latch moveable between a latched configuration wherein the second latch secures the cap to the other of the first and second housing components in the closed position and an unlatched configuration wherein the cap is moveable to the open position, and wherein the first latch is moveable from the latched configuration to the unlatched configuration only when the second latch is in the unlatched configuration.

11. The holding chamber of claim 10 wherein at least one or both of the first and second housing components comprises an engagement member disposed in the interior space, wherein the engagement member is adapted to engage a medicament delivery device disposed in the interior space, and wherein the interior space is dimensioned to receive the medicament delivery device when the first and second housing components are in the closed configuration.

12. The holding chamber of claim 11 wherein the engagement member comprises a first rib disposed on the first housing component, wherein the first rib is shaped and dimensioned to engage the medicament delivery device.

13. The holding chamber of claim 12 further comprising a second engagement member comprising a second rib disposed on the second housing component, wherein the second rib is shaped and dimensioned to engage the medicament delivery device.

14. The holding chamber of claim 10 further comprising a biasing member biasing the cap to the open position and maintaining the cap in the open position when the second latch is in the unlatched configuration.

15. A holding chamber configured to enclose and carry a pressurized metered dose inhaler, the holding chamber comprising:
- a first housing component comprising a user interface having an outlet opening; and
- a second housing component having an inlet opening spaced apart from the outlet opening of the first housing component, wherein the inlet opening comprises a sealable backpiece configured to receive a mouthpiece of the pressurized metered dose inhaler, wherein the first housing component is pivotally connected to the second housing component about a pivot axis, wherein the first and second housing components are pivotable relative to each other about the pivot axis between a closed configuration and an open configuration;
- a cap movably connected to one of the first and second housing component, wherein the cap is moveable between a closed position, wherein the cap engages the other of the first and second housing components and maintains the first and second housing components in the closed configuration, and an open position, wherein the first and second housing components are capable of being pivoted to the open configuration; and
- a biasing member maintaining the cap in the open position.

16. The holding chamber of claim 15 further comprising a first latch and a second latch, wherein the first latch is moveable between a latched configuration, wherein the first latch secures the cap to the other of the first and second housing components in the closed position, and an unlatched configuration, wherein the cap is moveable to the open position, and wherein the second latch is moveable between a latched configuration, wherein the second latch secures the first and second housing components in the closed configuration, and an unlatched configuration, wherein the first and second housing components are moveable to the open configuration.

17. The holding chamber of claim 16 wherein the second latch is moveable from the latched configuration to the unlatched configuration only when the first latch is in the unlatched configuration.

18. The holding chamber of claim 15 wherein at least one or both of the first and second housing components comprises an engagement member disposed in the interior space, wherein the engagement member is adapted to engage a medicament delivery device disposed in the interior space, and wherein the interior space is dimensioned to receive the medicament delivery device when the first and second housing components are in the closed configuration.

19. The holding chamber of claim 18 wherein the engagement member comprises a first rib disposed on the first housing component, wherein the first rib is shaped and dimensioned to engage the medicament delivery device.

20. The holding chamber of claim 19 further comprising a second engagement member comprising a second rib disposed on the second housing component, wherein the second rib is shaped and dimensioned to engage the medicament delivery device.

* * * * *